United States Patent
Larrick et al.

(10) Patent No.: US 11,078,276 B2
(45) Date of Patent: Aug. 3, 2021

(54) ANTI-CD79 ANTIBODIES AND THEIR USES

(71) Applicant: Nepenthe Bioscience LLC, Sunnvale, CA (US)

(72) Inventors: James Larrick, Sunnyvale, CA (US); Bo Yu, Sunnyvale, CA (US); Andrew Mendelsohn, Palo Alto, CA (US); John C. Cambier, Denver, CO (US)

(73) Assignee: Nepenthe Bioscience LLC, Sunnyvale, CA (US)

( * ) Notice: Subject to any disclaimer, the term of this patent is extended or adjusted under 35 U.S.C. 154(b) by 0 days.

(21) Appl. No.: 16/591,617

(22) Filed: Oct. 3, 2019

(65) Prior Publication Data

US 2020/0109198 A1     Apr. 9, 2020

Related U.S. Application Data

(60) Provisional application No. 62/740,655, filed on Oct. 3, 2018.

(51) Int. Cl.
   *C07K 16/28*     (2006.01)

(52) U.S. Cl.
   CPC ...... *C07K 16/2803* (2013.01); *C07K 2317/24* (2013.01); *C07K 2317/92* (2013.01)

(58) Field of Classification Search
   None
   See application file for complete search history.

(56) References Cited

U.S. PATENT DOCUMENTS

| | | | | |
|---|---|---|---|---|
| 6,180,370 | B1 * | 1/2001 | Queen | C07K 16/2866 435/69.6 |
| 10,981,987 | B2 * | 4/2021 | Chen | A61K 51/1027 |
| 2017/0066838 | A1 | 3/2017 | Pule et al. | |
| 2017/0204178 | A1 | 7/2017 | Finney et al. | |

FOREIGN PATENT DOCUMENTS

| | | |
|---|---|---|
| WO | WO 2016/090210 | 6/2016 |
| WO | WO 2017/214096 | 12/2017 |

OTHER PUBLICATIONS

Sela-Culang, Inbal et al. "The structural basis of antibody-antigen recognition." Frontiers in immunology vol. 4 302. Oct. 8, 2013, doi: 10.3389/fimmu.2013.00302 (Year: 2013).*
Rudikoff, S et al. "Single amino acid substitution altering antigen-binding specificity." Proceedings of the National Academy of Sciences of the United States of America vol. 79,6 (1982): 1979-83. doi:10.1073/pnas.79.6.1979 (Year: 1982).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
Hardy et al, Anti-CD79 antibody induces B-cell anergy that protects against autoimmunity, 2014, J. Immunol. vol. 192, pp. 1641-1650.

* cited by examiner

*Primary Examiner* — Michael Szperka
*Assistant Examiner* — Lia E Taylor
(74) *Attorney, Agent, or Firm* — HelixIP LLP

(57) ABSTRACT

The present disclosure provides humanized and affinity matured antibodies (mAbs) and fragments thereof that specifically bind to CD79 with high affinity. The anti-CD79 mAbs and fragments thereof can be used to treat antibody-associated conditions, including autoimmune diseases, allergies, transplant rejection, or immune-mediated rejection of a therapeutics optionally in combination with an additional therapeutic agent. Furthermore, the anti-CD79 mAbs and fragments thereof can be used for diagnostic purposes, including to detect CD79 cells in biological samples and to diagnose B-cell associated disorders.

13 Claims, 10 Drawing Sheets
Specification includes a Sequence Listing.

SEQUENCE LISTING

```
<160> NUMBER OF SEQ ID NOS: 77

<210> SEQ ID NO 1
<211> LENGTH: 119
<212> TYPE: PRT
<213> ORGANISM: Mus musculus

<400> SEQUENCE: 1

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Tyr Ser
            20                  25                  30

Trp Met Asn Trp Val Lys Gln Arg Pro Gly Lys Gly Leu Glu Trp Ile
        35                  40                  45

Gly Arg Ile Tyr Pro Glu Asn Gly Asp Thr Asn Tyr Asn Gly Lys Phe
    50                  55                  60

Lys Gly Lys Val Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Val Tyr Gly Tyr Pro His Phe Asp Tyr Trp Gly Gln Gly
            100                 105                 110

Thr Thr Leu Thr Val Ser Ser
        115

<210> SEQ ID NO 2
```

<211> LENGTH: 112
<212> TYPE: PRT
<213> ORGANISM: Mus musculus

<400> SEQUENCE: 2

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110

<210> SEQ ID NO 3
<211> LENGTH: 5
<212> TYPE: PRT
<213> ORGANISM: Mus musculus

<400> SEQUENCE: 3

Tyr Ser Trp Met Asn
1               5

<210> SEQ ID NO 4
<211> LENGTH: 17
<212> TYPE: PRT
<213> ORGANISM: Mus musculus

<400> SEQUENCE: 4

Arg Ile Tyr Pro Glu Asn Gly Asp Thr Asn Tyr Asn Gly Lys Phe Lys
1               5                   10                  15

Gly

<210> SEQ ID NO 5
<211> LENGTH: 10
<212> TYPE: PRT
<213> ORGANISM: Mus musculus

<400> SEQUENCE: 5

Trp Val Tyr Gly Tyr Pro His Phe Asp Tyr
1               5                   10

<210> SEQ ID NO 6
<211> LENGTH: 16
<212> TYPE: PRT
<213> ORGANISM: Mus musculus

<400> SEQUENCE: 6

Lys Ser Ser Gln Ser Leu Leu Asp Ser Asp Gly Lys Thr Tyr Leu Asn
1               5                   10                  15

<210> SEQ ID NO 7
<211> LENGTH: 7
<212> TYPE: PRT
<213> ORGANISM: Mus musculus

```
<400> SEQUENCE: 7

Leu Val Ser Lys Leu Asp Ser
1               5

<210> SEQ ID NO 8
<211> LENGTH: 9
<212> TYPE: PRT
<213> ORGANISM: Mus musculus

<400> SEQUENCE: 8

Trp Gln Gly Thr His Phe Pro Phe Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Humanized anitbody heavy chain

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Met
            35                  40                  45

Gly Arg Ile Tyr Pro Glu Asn Gly Asp Thr Asn Tyr Asn Gly Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Met
            35                  40                  45

Gly Arg Ile Tyr Pro Glu Asn Gly Asp Thr Asn Tyr Asn Gly Lys Phe
        50                  55                  60

Lys Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
```

```
                   100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Ile
            35                  40                  45

Gly Arg Ile Tyr Pro Glu Asn Gly Asp Thr Asn Tyr Asn Gly Lys Phe
        50                  55                  60

Lys Gly Arg Val Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
                100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Met
            35                  40                  45

Gly Arg Ile Tyr Pro Glu Asn Gly Asp Thr Asn Tyr Ala Gly Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
                100                 105                 110

Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
```

<223> OTHER INFORMATION: Humanized antibody heavy chain

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Ala Gly Lys Phe
    50                  55                  60

Lys Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115
```

<210> SEQ ID NO 14
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Ile
        35                  40                  45

Gly Arg Ile Tyr Pro Glu Asn Gly Asp Thr Asn Tyr Ala Gly Lys Phe
    50                  55                  60

Lys Gly Arg Val Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115
```

<210> SEQ ID NO 15
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
```

```
                35                  40                  45

Gly Arg Ile Tyr Pro Glu Ser Gly Asp Thr Asn Tyr Ala Gly Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
                100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Met
            35                  40                  45

Gly Arg Ile Tyr Pro Glu Ser Gly Asp Thr Asn Tyr Ala Gly Lys Phe
        50                  55                  60

Lys Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
                100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Humanized antibody heavy chain

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
                20                  25                  30

Trp Met Asn Trp Val Arg Gln Ala Pro Gly Gln Gly Leu Glu Trp Ile
            35                  40                  45

Gly Arg Ile Tyr Pro Glu Ser Gly Asp Thr Asn Tyr Ala Gly Lys Phe
        50                  55                  60

Lys Gly Arg Val Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: Humanized antibody light chain

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: Humanized antibody light chain

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Leu Gln Gln Arg Pro Gly Gln Ser
            35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Humanized antibody light chain

<400> SEQUENCE: 20

Asp Val Val Met Thr Gln Ser Pro Leu Ser Leu Pro Val Thr Leu Gly

```
                1               5                  10                 15
            Gln Pro Ala Ser Ile Ser Cys Lys Ser Ser Gln Ser Leu Leu Asp Ser
                           20                  25                  30

Asp Gly Lys Thr Tyr Leu Asn Trp Leu Gln Gln Arg Pro Gly Gln Ser
                        35                  40                  45

Pro Lys Arg Leu Ile Tyr Leu Val Ser Lys Leu Asp Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Trp Gln Gly
                            85                  90                  95

Thr His Phe Pro Phe Thr Phe Gly Gly Gly Thr Lys Val Glu Ile Lys
                           100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Humanized anitbody light chain

<400> SEQUENCE: 21

Asp Val Val Met Thr Gln Ser Pro Leu Ser Leu Pro Val Thr Leu Gly
            1               5                  10                 15

Gln Pro Ala Ser Ile Ser Cys Lys Ser Ser Gln Ser Leu Leu Asp Ser
                           20                  25                  30

Ser Gly Lys Thr Tyr Leu Asn Trp Phe Gln Gln Arg Pro Gly Gln Ser
                        35                  40                  45

Pro Arg Arg Leu Ile Tyr Leu Val Ser Lys Leu Asp Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Trp Gln Gly
                            85                  90                  95

Thr His Phe Pro Phe Thr Phe Gly Gly Gly Thr Lys Val Glu Ile Lys
                           100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Humanized antibody light chain

<400> SEQUENCE: 22

Asp Val Val Met Thr Gln Ser Pro Leu Ser Leu Pro Val Thr Leu Gly
            1               5                  10                 15

Gln Pro Ala Ser Ile Ser Cys Lys Ser Ser Gln Ser Leu Leu Asp Ser
                           20                  25                  30

Ser Gly Lys Thr Tyr Leu Asn Trp Leu Gln Gln Arg Pro Gly Gln Ser
                        35                  40                  45

Pro Arg Arg Leu Ile Tyr Leu Val Ser Lys Leu Asp Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Trp Gln Gly
                            85                  90                  95
```

```
Thr His Phe Pro Phe Thr Phe Gly Gly Gly Thr Lys Val Glu Ile Lys
            100                 105                 110
```

<210> SEQ ID NO 23
<211> LENGTH: 112
<212> TYPE: PRT
<213> ORGANISM: Artificial Sequence
<220> FEATURE:
<223> OTHER INFORMATION: Humanized antibody light chain

<400> SEQUENCE: 23

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Ser Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110
```

<210> SEQ ID NO 24
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Val Tyr Gly Tyr Pro His Phe Asp Tyr Trp Gly Gln Gly
            100                 105                 110

Thr Leu Val Thr Val Ser Ser
        115
```

<210> SEQ ID NO 25
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 25

```
Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Trp Val Tyr Gly Leu Pro His Phe Asp Tyr Trp Gly Gln Gly
                100                 105                 110

Thr Leu Val Thr Val Ser Ser
            115
```

<210> SEQ ID NO 26
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Trp Val Trp Gly Tyr Pro His Phe Asp Tyr Trp Gly Gln Gly
                100                 105                 110

Thr Leu Val Thr Val Ser Ser
            115
```

<210> SEQ ID NO 27
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60
```

```
Lys Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Trp Val Tyr Gly Tyr Pro His Leu Asp Tyr Trp Gly Gln Gly
            100                 105                 110

Thr Leu Val Thr Val Ser Ser
            115
```

<210> SEQ ID NO 28
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 28

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Gln Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Ile Pro Phe Thr Phe Gly Gly Gly Thr Lys Val Glu Ile Lys
            100                 105                 110
```

<210> SEQ ID NO 29
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 29

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Gln Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Val Pro Phe Thr Phe Gly Gly Gly Thr Lys Val Glu Ile Lys
            100                 105                 110
```

<210> SEQ ID NO 30
<211> LENGTH: 112
<212> TYPE: PRT
<213> ORGANISM: Artificial Sequence

```
<220> FEATURE:
<223> OTHER INFORMATION: Affinity matured antibody light chain

<400> SEQUENCE: 30

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Leu Pro Phe Thr Phe Gly Gly Gly Thr Lys Val Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 31

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Arg Pro Phe Thr Phe Gly Gly Gly Thr Lys Val Glu Ile Lys
            100                 105                 110

<210> SEQ ID NO 32
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60
```

```
Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Tyr Pro His Phe Asp Tyr Trp Gly Gln Gly
            100                 105                 110

Thr Leu Val Thr Val Ser Ser
            115
```

<210> SEQ ID NO 33
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 33

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Gly Tyr Ser
             20                  25                  30

Trp Met Asn Trp Val Arg Gln Ala Pro Gly Gln Gly Leu Glu Trp Met
         35                  40                  45

Gly Arg Ile Tyr Pro Glu Asn Gly Asp Thr Asn Tyr Asn Gly Lys Phe
     50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Tyr Pro His Phe Asp Tyr Trp Gly Gln Gly
            100                 105                 110

Thr Leu Val Thr Val Ser Ser
            115
```

<210> SEQ ID NO 34
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 34

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Ser Tyr Ser
             20                  25                  30

Trp Met Asn Trp Val Arg Gln Ala Pro Gly Gln Gly Leu Glu Trp Met
         35                  40                  45

Gly Arg Ile Tyr Pro Glu Asn Gly Asp Thr Asn Tyr Asn Gly Lys Phe
     50                  55                  60

Lys Gly Arg Val Thr Met Thr Arg Asp Thr Ser Ile Ser Thr Ala Tyr
 65                  70                  75                  80

Met Glu Leu Ser Arg Leu Arg Pro Asp Asp Thr Ala Val Tyr Tyr Cys
                 85                  90                  95

Ala Arg Trp Val Tyr Gly Tyr Pro His Phe Asp Tyr Trp Gly Gln Gly
            100                 105                 110

Thr Leu Val Thr Val Ser Ser
            115
```

<210> SEQ ID NO 35
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 35

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ala Phe Asn Tyr Ser
            20                  25                  30

Trp Met Asn Trp Val Arg Gln Val Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115
```

<210> SEQ ID NO 36
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 36

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115
```

<210> SEQ ID NO 37
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Val Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 38
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 39
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Asn Tyr Ser
            20                  25                  30

Trp Val Asn Trp Val Arg Gln Ala Pro Gly Gln Gly Phe Glu Trp Met
        35                  40                  45

Gly Arg Ile Tyr Pro Glu Asn Gly Asp Thr Asn Tyr Asn Gly Lys Phe
    50                  55                  60

```
Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 40

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Arg Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Gly Thr Asn Tyr Asn Gly Lys Phe
    50                  55                  60

Lys Gly Arg Val Thr Met Thr Met Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 41

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Asn Gly Asp Thr Asn Tyr Asn Gly Lys Phe
    50                  55                  60

Arg Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Tyr Pro His Phe Asp Tyr Trp Gly Gln Gly
            100                 105                 110

Thr Leu Val Thr Val Ser Ser
```

```
<210> SEQ ID NO 42
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 42

Asp Val Val Met Thr Gln Ser Pro Leu Ser Leu Pro Val Thr Leu Gly
1               5                   10                  15

Leu Pro Ala Ser Ile Ser Cys Lys Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Lys Ser Ser Lys Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 44
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30
```

Asp Gly Lys Thr Tyr Leu Asn Trp Leu Gln Gln Arg Pro Gly Gln Ser
            35                  40                  45

Pro Arg Arg Ile Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 45

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
            35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Trp Gln Gly
                85                  90                  95

Thr His Leu Pro Phe Thr Phe Gly Gly Gly Thr Lys Val Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 46

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
            35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Trp Gln Gly
                85                  90                  95

Thr His Leu Pro Phe Thr Phe Gly Gly Gly Thr Lys Val Glu Ile Lys
            100                 105                 110

-continued

```
<210> SEQ ID NO 47
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 47

Asp Val Val Met Thr Gln Ser Pro Leu Ser Leu Pro Val Thr Leu Gly
1               5                   10                  15

Gln Thr Ala Ser Ile Ser Cys Lys Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Leu Pro Phe Thr Phe Gly Gly Gly Thr Lys Val Glu Ile Lys
            100                 105                 110

<210> SEQ ID NO 48
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 48

Asp Val Val Met Thr Gln Ser Pro Leu Ser Leu Pro Val Thr Leu Gly
1               5                   10                  15

Arg Pro Ala Ser Ile Ser Cys Lys Ser Gln Ser Leu Leu Asp Ser
            20                  25                  30

Gly Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 49
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 49

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Asp Ser
            20                  25                  30

Asp Gly Lys Thr Tyr Leu Asn Trp Leu Gln Gln Arg Pro Gly Gln Ser
        35                  40                  45
```

Pro Arg Arg Leu Ile Tyr Leu Val Ser Lys Leu Asp Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
                100                 105                 110

<210> SEQ ID NO 50
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 50

Asp Val Val Met Thr Gln Ser Pro Leu Ser Leu Pro Val Thr Leu Gly
 1               5                  10                  15

Leu Pro Ala Ser Ile Ser Cys Lys Ser Ser Gln Ser Leu Leu Asp Thr
            20                  25                  30

Asp Gly Lys Thr Tyr Leu Asn Trp Leu Gln Gln Arg Pro Gly Gln Ser
            35                  40                  45

Pro Arg Arg Leu Ile Tyr Leu Val Ser Lys Leu Asp Ser Gly Val Pro
            50                  55                  60

Asp Arg Phe Ile Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
                100                 105                 110

<210> SEQ ID NO 51
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 51

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Pro
            35                  40                  45

Pro Arg Arg Leu Ile Tyr Leu Val Ser Lys Leu Asp Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
                100                 105                 110

<210> SEQ ID NO 52
<211> LENGTH: 112
<212> TYPE: PRT

<213> ORGANISM: Artificial Sequence
<220> FEATURE:
<223> OTHER INFORMATION: Affinity matured antibody light chain

<400> SEQUENCE: 52

Asp Val Val Met Thr Gln Ser Pro Leu Ser Leu Pro Val Thr Leu Gly
1               5                   10                  15

Gln Pro Ala Ser Ile Thr Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Pro Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 53

Asp Val Val Met Thr Gln Ser Pro Pro Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Val Pro Phe Thr Phe Gly Gly Gly Thr Lys Val Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 54

Asp Val Val Met Thr Gln Ser Pro Leu Ser Leu Pro Val Thr Leu Gly
1               5                   10                  15

Gln Thr Ala Ser Ile Ser Cys Lys Ser Ser Gln Ser Leu Leu Asp Arg
            20                  25                  30

Asp Gly Lys Thr Tyr Leu Asn Trp Leu Gln Gln Arg Pro Gly Gln Ser
        35                  40                  45

Pro Arg Arg Ile Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 55
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 55

Asp Val Val Met Thr Gln Ser Pro Leu Ser Met Pro Val Thr Leu Gly
1               5                   10                  15

Leu Pro Ala Ser Ile Ser Cys Lys Ser Ser Gln Ser Leu Leu Asp Ser
            20                  25                  30

His Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 56

Asp Val Val Met Thr Gln Ser Pro Leu Ser Leu Pro Val Thr Leu Gly
1               5                   10                  15

Leu Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ile Pro Phe Thr Phe Ser Gly Gly Thr Lys Val Glu Ile Lys
            100                 105                 110

<210> SEQ ID NO 57
<211> LENGTH: 16
<212> TYPE: PRT
<213> ORGANISM: Artificial Sequence
<220> FEATURE:
<223> OTHER INFORMATION: Antibody light chain CDR1

<400> SEQUENCE: 57

Lys Ser Ser Gln Ser Leu Leu Asp Ser Ser Gly Lys Thr Tyr Leu Asn
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Antibody heavy chain CDR2

<400> SEQUENCE: 58

Arg Ile Tyr Pro Glu Asn Gly Asp Thr Asn Tyr Ala Gly Lys Phe Lys
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: Antibody heavy chain CDR2

<400> SEQUENCE: 59

Arg Ile Tyr Pro Glu Ser Gly Asp Thr Asn Tyr Ala Gly Lys Phe Lys
1               5                   10                  15

Gly

<210> SEQ ID NO 60
<211> LENGTH: 15
<212> TYPE: PRT
<213> ORGANISM: Artificial Sequence
<220> FEATURE:
<223> OTHER INFORMATION: Antibody light chain FR2

<400> SEQUENCE: 60

Trp Phe Gln Gln Arg Pro Gly Gln Ser Pro Arg Arg Leu Ile Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Antibody light chain FR2

<400> SEQUENCE: 61

Trp Leu Gln Gln Arg Pro Gly Gln Ser Pro Arg Arg Leu Ile Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Antibody light chain FR2

<400> SEQUENCE: 62

Trp Leu Gln Gln Arg Pro Gly Gln Ser Pro Lys Arg Leu Ile Tyr
1               5                   10                  15

<210> SEQ ID NO 63
<211> LENGTH: 30
<212> TYPE: PRT

```
<213> ORGANISM: Artificial Sequence
<220> FEATURE:
<223> OTHER INFORMATION: Antibody heavy chain FR1

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser
            20                  25                  30

<210> SEQ ID NO 64
<211> LENGTH: 14
<212> TYPE: PRT
<213> ORGANISM: Artificial Sequence
<220> FEATURE:
<223> OTHER INFORMATION: Antibody heavy chain FR2

<400> SEQUENCE: 64

Trp Val Arg Gln Ala Pro Gly Gln Gly Leu Glu Trp Met Gly
1               5                   10

<210> SEQ ID NO 65
<211> LENGTH: 32
<212> TYPE: PRT
<213> ORGANISM: Artificial Sequence
<220> FEATURE:
<223> OTHER INFORMATION: Antibody heavy chain FR3

<400> SEQUENCE: 65

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Antibody heavy chain FR3

<400> SEQUENCE: 66

Arg Val Thr Met Thr Ala Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 67
<211> LENGTH: 14
<212> TYPE: PRT
<213> ORGANISM: Artificial Sequence
<220> FEATURE:
<223> OTHER INFORMATION: Antibody heavy chain FR2

<400> SEQUENCE: 67

Trp Val Arg Gln Ala Pro Gly Gln Gly Leu Glu Trp Ile Gly
1               5                   10

<210> SEQ ID NO 68
<211> LENGTH: 32
<212> TYPE: PRT
<213> ORGANISM: Artificial Sequence
<220> FEATURE:
<223> OTHER INFORMATION: Antibody heavy chain FR3

<400> SEQUENCE: 68
```

Arg Val Thr Leu Thr Ala Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 69
<211> LENGTH: 1415
<212> TYPE: DNA
<213> ORGANISM: Artificial Sequence
<220> FEATURE:
<223> OTHER INFORMATION: Chimeric antigen receptor

<400> SEQUENCE: 69

```
gatgttgtga tgactcagtc tccactctcc ctgcccgtca cccttggaca gccggcctcc    60
atctcctgca gtcaagtca gagcctctta gatagtgatg aaagacata tttgaattgg    120
ttacagcaga ggccaggcca atctccaagg cgcctaattt atctggtgtc taaactggac    180
tctggggtcc cagacagatt cagcggcagt gggtcaggca ctgatttcac actgaaaatc    240
agcagggtgg aagctgagga tgttggggtt tattactgct ggcaaggtac acatctgcca    300
ttcacgttcg gcggagggac caaggtggag atcaaaggtg gcggtggctc gggcggtggt    360
gggtcgggtg gcggcggatc tcaggtgcag ctggtgcagt ctggggctga ggtgaagaag    420
cctgggcct cagtgaaggt ctcctgcaag gcttctggat acgcattcag ttactcctgg    480
atgaactggg tgcgacaggc cctggacaa gggcttgagt ggatgggacg gatttatcct    540
gaaaatggag atactaacta caatgggaag ttcaagggca gggtcaccat gaccagggac    600
acgtccatca gcacagccta catggagctg agcaggctga gatctgacga cacggccgtg    660
tattactgtg cgagatgggt ctatggtctt ccccactttg actactgggg ccaaggaacc    720
ctggtcaccg tctcctcagc tagcaccacg acgccagcgc gcgaccacc aacaccggcg    780
cccaccatcg cgtcgcagcc cctgtccctg cgcccagagg cgtgccggcc agcggcgggg    840
ggcgcagtgc acacgagggg gctggacttc gcctgtgata tctacatctg ggcgcccttg    900
gccgggactt gtggggtcct tctcctgtca ctggttatca cccttactg caaacggggc    960
agaaagaaac tcctgtatat attcaaacaa ccatttatga gaccagtaca aactactcaa   1020
gaggaagatg gctgtagctg ccgatttcca gaagaagaag aaggaggatg tgaactgaga   1080
gtgaagttca gcaggagcgc agacgccccg cgtacaagca gggccagaac cagctctata   1140
acgagctcaa tctaggacga agagaggagt acgatgtttt ggacaagaga cgtggccggg   1200
accctgagat gggggaaag ccgagaagga agaacccca ggaaggcctg tacaatgaac   1260
tgcagaaaga taagatggcg gaggcctaca gtgagattgg gatgaaaggc gagcgccgga   1320
ggggcaaggg gcacgatggc ctttaccagg gtctcagtac agccaccaag gacacctacg   1380
acgcccttca catgcaggcc ctgccccctc gctga                              1415
```

<210> SEQ ID NO 70
<211> LENGTH: 470
<212> TYPE: PRT
<213> ORGANISM: Artificial Sequence
<220> FEATURE:
<223> OTHER INFORMATION: Chimeric antigen receptor

<400> SEQUENCE: 70

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser

```
                 20                  25                  30
Asp Gly Lys Thr Tyr Leu Asn Trp Leu Gln Gln Arg Pro Gly Gln Ser
                 35                  40                  45

Pro Arg Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ser
 65                  70                  75                  80

Arg Val Glu Ala Glu Asp Val Gly Val Tyr Tyr Cys Trp Gln Gly Thr
                 85                  90                  95

His Leu Pro Phe Thr Phe Gly Gly Thr Lys Val Glu Ile Lys Gly
                100                 105                 110

Gly Gly Gly Ser Gly Gly Gly Gly Ser Gly Gly Gly Gly Ser Gln Val
                115                 120                 125

Gln Leu Val Gln Ser Gly Ala Glu Val Lys Lys Pro Gly Ala Ser Val
                130                 135                 140

Lys Val Ser Cys Lys Ala Ser Gly Tyr Ala Phe Ser Tyr Ser Trp Met
145                 150                 155                 160

Asn Trp Val Arg Gln Ala Pro Gly Gln Gly Leu Glu Trp Met Gly Arg
                165                 170                 175

Ile Tyr Pro Glu Asn Gly Asp Thr Asn Tyr Asn Gly Lys Phe Lys Gly
                180                 185                 190

Arg Val Thr Met Thr Arg Asp Thr Ser Ile Ser Thr Ala Tyr Met Glu
                195                 200                 205

Leu Ser Arg Leu Arg Ser Asp Asp Thr Ala Val Tyr Tyr Cys Ala Arg
                210                 215                 220

Trp Val Tyr Gly Leu Pro His Phe Asp Tyr Trp Gly Gln Gly Thr Leu
225                 230                 235                 240

Val Thr Val Ser Ser Ala Ser Thr Thr Thr Pro Ala Pro Arg Pro Pro
                245                 250                 255

Thr Pro Ala Pro Thr Ile Ala Ser Gln Pro Leu Ser Leu Arg Pro Glu
                260                 265                 270

Ala Cys Arg Pro Ala Ala Gly Gly Ala Val His Thr Arg Gly Leu Asp
                275                 280                 285

Phe Ala Cys Asp Ile Tyr Ile Trp Ala Pro Leu Ala Gly Thr Cys Gly
                290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
                340                 345                 350

Glu Gly Gly Cys Glu Leu Arg Val Lys Phe Ser Arg Ser Ala Asp Ala
                355                 360                 365

Pro Ala Tyr Lys Gln Gly Gln Asn Gln Leu Tyr Asn Glu Leu Asn Leu
                370                 375                 380

Gly Arg Arg Glu Glu Tyr Asp Val Leu Asp Lys Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
                420                 425                 430

Gly Met Lys Gly Glu Arg Arg Arg Gly Lys Gly His Asp Gly Leu Tyr
                435                 440                 445
```

```
Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 71
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Asn Tyr Ser
            20                  25                  30

Trp Val Asn Trp Val Arg Gln Ala Pro Gly Gln Gly Phe Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Asn Tyr Ser
            20                  25                  30

Trp Val Asn Trp Val Arg Gln Ala Pro Gly Gln Gly Phe Glu Trp Met
        35                  40                  45

Gly Arg Ile Tyr Pro Glu Asn Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Val Tyr Gly Tyr Pro His Phe Asp Tyr Trp Gly Gln Gly
            100                 105                 110

Thr Leu Val Thr Val Ser Ser
        115

<210> SEQ ID NO 73
<211> LENGTH: 112
<212> TYPE: PRT
```

<213> ORGANISM: Artificial Sequence
<220> FEATURE:
<223> OTHER INFORMATION: Affinity matured antibody light chain

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Leu Pro Phe Thr Phe Gly Gly Gly Thr Lys Val Glu Ile Lys
            100                 105                 110

<210> SEQ ID NO 74
<211> LENGTH: 112
<212> TYPE: PRT
<213> ORGANISM: Artificial Sequence
<220> FEATURE:
<223> OTHER INFORMATION: Affinity matured antibody light chain

<400> SEQUENCE: 74

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Leu Pro Phe Thr Phe Gly Gly Gly Thr Lys Val Glu Ile Lys
            100                 105                 110

<210> SEQ ID NO 75
<211> LENGTH: 119
<212> TYPE: PRT
<213> ORGANISM: Artificial Sequence
<220> FEATURE:
<223> OTHER INFORMATION: Affinity matured antibody heavy chain

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Tyr Pro Glu Ser Gly Asp Thr Asn Tyr Asn Gly Lys Phe
    50                  55                  60

```
Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Leu Pro His Phe Asp Tyr Trp Gly Gln Gly
            100                 105                 110

Thr Leu Val Thr Val Ser Ser
        115
```

<210> SEQ ID NO 76
<211> LENGTH: 119
<212> TYPE: PRT
<213> ORGANISM: Artificial Sequence
<220> FEATURE:
<223> OTHER INFORMATION: Antibody heavy chain

<400> SEQUENCE: 76

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Ser Tyr Ser
                 20                  25                  30

Trp Met Asn Trp Val Arg Gln Ala Pro Gly Gln Gly Leu Glu Trp Met
             35                  40                  45

Gly Arg Ile Tyr Pro Glu Asn Gly Asp Thr Asn Tyr Ala Gly Lys Phe
         50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Val Tyr Gly Leu Pro His Phe Asp Tyr Trp Gly Gln Gly
            100                 105                 110

Thr Leu Val Thr Val Ser Ser
        115
```

<210> SEQ ID NO 77
<211> LENGTH: 119
<212> TYPE: PRT
<213> ORGANISM: Artificial Sequence
<220> FEATURE:
<223> OTHER INFORMATION: Antibody heavy chain

<400> SEQUENCE: 77

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Ser Tyr Ser
                 20                  25                  30

Trp Met Asn Trp Val Arg Gln Ala Pro Gly Gln Gly Leu Glu Trp Met
             35                  40                  45

Gly Arg Ile Tyr Pro Glu Ser Gly Asp Thr Asn Tyr Ala Gly Lys Phe
         50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95
```

```
Ala Arg Trp Val Tyr Gly Leu Pro His Phe Asp Tyr Trp Gly Gln Gly
            100                 105                 110

Thr Leu Val Thr Val Ser Ser
        115
```

ANTI-CD79 ANTIBODIES AND THEIR USES

STATEMENT AS TO FEDERALLY SPONSORED RESEARCH

This invention was made with government support under Grant No. 1R43AI120433-01 awarded by the government agency National Institute of Allergy and Infectious Diseases (NIAID). The government has certain rights in the invention.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "PRI011_ST25.txt", a creation date of Sep. 30, 2019, and a size of 73 kilobytes. The Sequence Listing filed via EFS-Web is part of the specification and is incorporated in its entirety by reference herein.

BACKGROUND OF THE DISCLOSURE

B cells play a major role in the pathogenesis of many autoimmune disorders, including rheumatoid arthritis (RA), systemic lupus erythematosus (SLE), multiple sclerosis, and type I diabetes mellitus (T1D), as indicated by the efficacy of B cell-targeted therapies, e.g. rituximab, in these diseases. Unfortunately, current therapies are predicated on B-cell depletion, which is problematic from a safety standpoint. Due to consequent immunosuppression, existing standard-of-care therapies generate adverse effects, notably opportunistic infections and activation of viruses from latency, due to long-term, severe B cell depletion.

CD79 (Cluster of Differentiation 79) is a transmembrane protein that forms a complex with the B-cell receptor (BCR) and generates a signal following recognition of antigen by the BCR. CD79 is composed of two distinct chains called CD79A and CD79B (formerly known as Ig-alpha and Ig-beta); these form a heterodimer on the surface of a B cell stabilized by disulfide bonding. CD79a and CD79b are both members of the immunoglobulin superfamily. CD79 has been used as a pan-B cell marker, and can be used for the detection of B-cell neoplasms.

Unlike anti-CD20 mAbs, the protective effects of CD79-targeted mAbs do not require cell depletion; rather, they act by inducing a reversible unresponsive or anergic state, and thus do not participate in immune response generation. In animal models, anti-CD79 antibodies have provided immunosuppression and reduced inflammation by inducing anergy in B cells.

SUMMARY OF THE DISCLOSURE

The present disclosure provides antibodies, including fragments thereof that specifically bind to CD79 with high affinity. The antibodies can be monoclonal, and can be chimeric or humanized antibodies. Chimeric anti-CD79 antibodies including fragments thereof may have non-human (e.g., murine) complementarity-determining regions (CDRs) and non-human framework region(s), and optionally one or more human constant domains. Non-human, heavy and light chain variable regions include SEQ ID NOs: 1-2. Humanized anti-CD79 antibodies including fragments thereof may have non-human (e.g., murine) CDRs and human framework region(s), and optionally non-human framework amino acid residues adjacent to CDRs and optionally one or more human constant domains. Non-human CDRs include, for example, VH CDR1-3 of SEQ ID NOs: 3-5 and VL-CDR1-3 of SEQ ID NOs: 6-8.

The humanized antibodies disclosed represent anti-CD79 antibodies obtained from grafting the CDRs of SEQ ID NOs 3-8 into a human framework for a heavy chain and a human framework for a light chain, along with a select number of framework residues from the mouse antibody. Nine variable regions for humanized heavy chains (SEQ ID NOs: 9-17) and six variable regions for humanized light chains (SEQ ID NOs: 18-23) can be combined to make anti-CD79 humanized antibodies. Anti-CD79 antibodies disclosed herein also include those obtained from an affinity maturation library made from a humanized anti-CD79 antibody. An anti-CD79 antibody can be made with a heavy chain variable region selected from SEQ ID NOs: 9-17, 24-27, 32-41, 71, 72, and 75-77, and a light chain variable region selected from SEQ ID NOs: 18-23, 28-31, 42-56, and 73-74. An anti-CD79 antibody can also include a heavy chain variable region that has 99%, 95%, 90%, 80% or 70% sequence identity with one of SEQ ID NOs: 9-17, 24-27, 32-41, 71, 72, and 75-77, and a light chain variable region that has 99%, 95%, 90%, 80% or 70% sequence identity with one of SEQ ID NOs: 18-23, 28-31, 42-56, and 73-74. An anti-CD79 antibody can bind to CD79 with an affinity of 2.0-5.1 nM, or 45 nM to 300 nM, or 2.0 to 300 nM. An anti-CD79 antibody can bind with an affinity of at least 300 nM, or at least 140 nM, or at least 100 nM, or at least 5.1 nm, at least 3.8 nM, or at least 2.4 nM.

The anti-CD79 antibodies described herein may include modifications that provide a desired property to the antibody. For example, modifications can increase the serum half-life of the antibody or the modification can decrease serum half-life. The modification can also increase or decrease the effector function of the antibody. The modification could decrease immunogenicity, or reduce other unwanted side effects or adverse events caused by the anti-CD79 antibodies.

The anti-CD79 antibodies described herein can induce an anergic state in the B-cells of a subject, and thus can be used to treat certain autoimmune diseases. For example, autoimmune diseases associated with anti-self antibody reactions can be treated with the anti-CD79 antibodies as the anergic state induced will prevent the anti-self antibodies from being produced. The anti-CD79 antibodies described herein also can be used to induce an anergic state in any condition that has an undesired antibody response. The anti-CD79 antibodies described herein can be used to induce an anergic state in B-cells. The anti-CD79 antibodies described herein can be used to inhibit the proliferation of B-cells. The anti-CD79 antibodies described herein can be used to prevent infusion reactions resulting from pre-existing anti-drug antibodies. The anti-CD79 antibodies described herein can be used to prevent the formation of anti-drug antibodies following injection of a biologic therapy. Undesired antibody-associated conditions can include, for example, autoimmune disease, certain allergies (antibody associated allergies), certain kinds of type I diabetes, etc. Autoimmune disease that can be treated with the anti-CD79 antibodies include, for example, systemic lupus erythematosus (SLE), inflammatory bowel disease (e.g., Crohn's disease and ulcerative colitis), rheumatoid arthritis, multiple sclerosis, Grave's disease, CREST syndrome, systemic sclerosis, celiac disease, etc. Other autoimmune diseases include, for example, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosis, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease. These undesired antibody-associated conditions can be treated by administering one or more of the anti-CD79 antibodies described herein to a subject suffering from the undesired antibody-associated condition.

The anti-CD79 antibodies described herein can be used to treat CD79 positive hematopoietic cancers such lymphomas and leukemias. They can also be used in chimeric antigen receptors (CAR) to make immune cells with an anti-CD79 CARs. These anti-CD79 CAR immune cells include, for example, T-cells or natural killer cells with the anti-CD79 CAR. The anti-CD79 CAR T-cells and/or natural killer cells can be used to treat diseases where the disease causing cell displays CD79. Such diseases include, for example, CD79 positive hematopoietic cancers such as lymphomas and leukemias.

BRIEF DESCRIPTION OF THE DRAWINGS

A better understanding of features and advantages of the present disclosure will be obtained by reference to the following detailed description, which sets forth illustrative embodiments of the disclosure, and the accompanying drawings.

DETAILED DESCRIPTION OF THE DISCLOSURE

Figure 1:
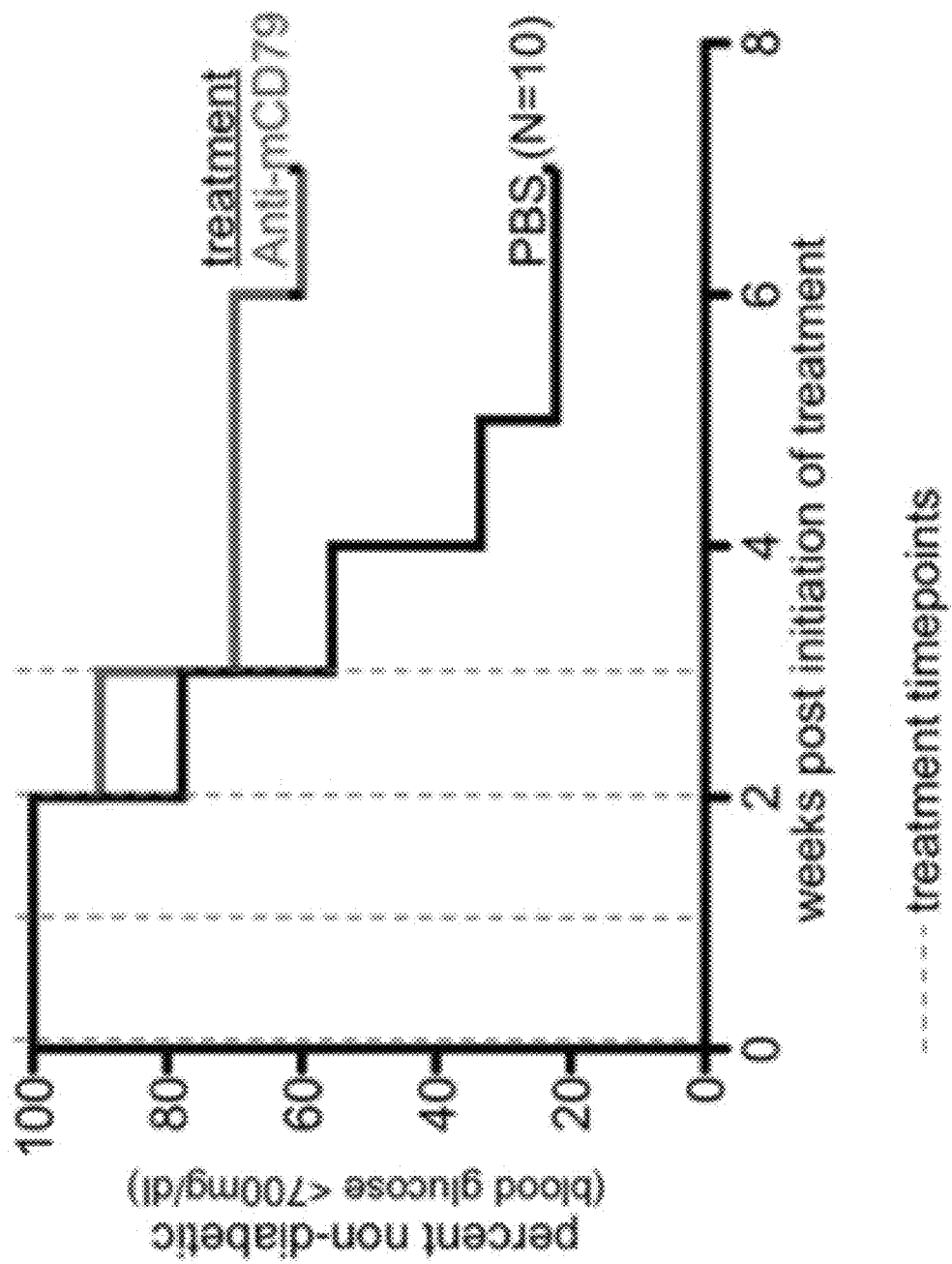
FIG. 1 is a graph showing the development of type 1 diabetes in VH125NOD mice over time.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein can be employed in practicing the disclosure. It is also understood that every embodiment of the disclosure can optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act or step, the order of the acts or steps of the method is not necessarily limited to the order in which the acts or steps of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

It is further understood that reference to a peptide, a polypeptide or a protein herein, such as an antibody or a fragment thereof, includes pharmaceutically acceptable salts thereof unless specifically stated otherwise or the context clearly indicates otherwise. Such salts can have a positive net charge, a negative net charge or no net charge.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

Definitions

Unless defined otherwise or clearly indicated otherwise by their use herein, all technical and scientific terms used herein have the same meaning as commonly understood by those of ordinary skill in the art to which this application belongs.

As used in the specification and the appended claims, the indefinite articles "a" and "an" and the definite article "the" can include plural referents as well as singular referents unless specifically stated otherwise or the context clearly indicates otherwise.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within ±10%, 5%, 4%, 3%, 2% or 1% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

The term "antibody" refers to a protein functionally defined as a binding protein and structurally defined as comprising an amino acid sequence that is recognized as being derived from the framework region of an immunoglobulin encoding gene. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical gamma immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments. Thus, for example, pepsin digests an antibody below the disulfide linkages in the hinge region to produce F(ab)'$_2$, a dimer of Fab' which itself is naturally a light chain joined to VH-CH1-Hinge by a disulfide bond. The F(ab)'$_2$ may be reduced under mild conditions to break the disulfide linkage/s in the hinge region thereby converting the (Fab')$_2$ dimer into an Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill in the art will appreciate that fragments can be synthesized de novo either chemically or by utilizing recombinant DNA methods. Thus, the term antibody, as used herein also includes antibody fragments either produced by the modification of whole antibodies or synthesized using recombinant DNA methodologies. Preferred antibodies include $V_H$—$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988, which is hereby incorporated by reference in its entirety). While the $V_H$ and $V_L$ are connected to each as a single polypeptide chain, the $V_H$ and $V_L$ domains associate non-covalently. Alternatively, the antibody can be another fragment. Other fragments can also be generated, including using recombinant techniques. For example Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage to one of the chains of g3p (see, e.g., U.S. Pat. No. 5,733,743, which is hereby incorporated by reference in its entirety). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778, all of which are hereby incorporated by reference in their entirety). Particularly preferred antibodies include all those that have been displayed on phage or generated by recombinant technology using vectors where the chains are secreted as soluble proteins, e.g., scFv, Fv, Fab, (Fab')$_2$. Antibodies can also include diabodies and minibodies.

Antibodies also include heavy chain dimers, such as antibodies from camelids. Since the V$_H$ region of a heavy chain dimer IgG in a camelid does not have to make hydrophobic interactions with a light chain, the region in the heavy chain that normally contacts a light chain is changed to hydrophilic amino acid residues in a camelid. V$_H$ domains of heavy-chain dimer IgGs are called V$_{HH}$ domains.

In camelids, the diversity of antibody repertoire is determined by the complementary determining regions (CDR) 1, 2, and 3 in the V$_H$ or V$_{HH}$ regions. The CDR3 in the camel V$_{HH}$ region is characterized by its relatively long length averaging 16 amino acids (Muyldermans et al., 1994, Protein Engineering 7(9): 1129, which is hereby incorporated by reference in its entirety). This is in contrast to CDR3 regions of antibodies of many other species. For example, the CDR3 of mouse V$_H$ has an average of 9 amino acids.

Libraries of camelid-derived antibody variable regions, which maintain the in vivo diversity of the variable regions of a camelid, can be made by, for example, the methods disclosed in U.S. Patent Application publication No. US20050037421, published Feb. 17, 2005, which is hereby incorporated by reference in its entirety.

As used herein, the term "binding specificity" of an antibody refers to the identity of the antigen to which the antibody binds, preferably to the identity of the epitope to which the antibody binds.

As used herein, the term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

As used herein, the term "complementarity-determining region" or "CDR" refer to the art-recognized term as exemplified by Kabat and Chothia. CDRs are also generally known as hypervariable regions or hypervariable loops (Chothia and Lesk (1987) J Mol. Biol. 196: 901; Chothia et al. (1989) Nature 342: 877; E. A. Kabat et al., Sequences of Proteins of Immunological Interest (National Institutes of Health, Bethesda, Md.) (1987); and Tramontano et al. (1990) J Mol. Biol. 215: 175, all of which are hereby incorporated by reference in their entirety). "Framework region" or "FR" refers to the region of the V domain that flank the CDRs. The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol). 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. Jan. 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996, all of which are hereby incorporated by reference in their entirety).

Whenever the term "at least" or "greater than" precedes the first numerical value in a series of two or more numerical values, the term "at least" or "greater than" applies to each one of the numerical values in that series of numerical values.

The term "heterologous" refers to an amino acid or nucleotide sequence that is not naturally found in association with the amino acid or nucleotide sequence with which it is associated.

Whenever the term "no more than" or "less than" precedes the first numerical value in a series of two or more numerical values, the term "no more than" or "less than" applies to each one of the numerical values in that series of numerical values.

The term "polynucleotide" refers to a polymer composed of nucleotide units. Polynucleotides include naturally occurring nucleic acids, such as deoxyribonucleic acid ("DNA") and ribonucleic acid ("RNA"), as well as nucleic acid analogs. Nucleic acid analogs include those which contain non-naturally occurring bases, nucleotides that engage in linkages with other nucleotides other than the naturally occurring phosphodiester bond, or/and bases attached through linkages other than phosphodiester bonds. Non-limiting examples of nucleotide analogs include phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, e.g., using an automated DNA synthesizer. The term "nucleic acid molecule" typically refers to larger polynucleotides. The term "oligonucleotide" typically refers to shorter polynucleotides. In certain embodiments, an oligonucleotide contains no more than about 50 nucleotides. It is understood that when a nucleotide sequence is represented by a DNA sequence (i.e., A, T, G, C), this also includes an RNA sequence (i.e., A, U, G, C) in which "U" replaces "T".

The term "polypeptide" refers to a polymer composed of natural or/and unnatural amino acid residues, naturally occurring structural variants thereof, or/and synthetic non-naturally occurring analogs thereof, linked via peptide bonds. Synthetic polypeptides can be synthesized, e.g., using an automated polypeptide synthesizer. Polypeptides can also be produced recombinantly in cells expressing nucleic acid sequences that encode the polypeptides. The term "protein" typically refers to larger polypeptides. The term "peptide" typically refers to shorter polypeptides. In certain embodiments, a peptide contains no more than about 50, 40 or 30 amino acid residues. Polypeptides include antibodies and fragments thereof. Conventional notation is used herein to portray polypeptide sequences: the left-hand end of a polypeptide sequence is the amino (N)-terminus; the right-hand end of a polypeptide sequence is the carboxyl (C)-terminus.

Polypeptides can include one or more modifications that may be made during the course of synthetic or cellular production of the polypeptide, such as one or more post-translational modifications, whether or not the one or more modifications are deliberate. Modifications can include without limitation glycosylation (e.g., N-linked glycosylation and O-linked glycosylation), lipidation, phosphorylation, sulfation, acetylation (e.g., acetylation of the N-terminus), amidation (e.g., amidation of the C-terminus), hydroxylation, methylation, formation of an intramolecular or intermolecular disulfide bond, formation of a lactam between two side chains, formation of pyroglutamate, and ubiquitination. As another example, a polypeptide can be attached to a natural polymer (e.g., a polysaccharide) or a synthetic polymer (e.g., polyethylene glycol [PEG]), lipidated (e.g., acylated with a $C_8$-$C_{20}$ acyl group), or labeled with a detectable agent (e.g., a radionuclide, a fluorescent dye or an enzyme). PEGylation can increase the protease resistance, stability and half-life, increase the solubility and reduce the aggregation of the polypeptide.

The term "conservative substitution" refers to substitution of an amino acid in a polypeptide with a functionally, structurally or chemically similar natural or unnatural amino acid. In certain embodiments, the following groups each contain natural amino acids that are conservative substitutions for one another:

1) Glycine (Gly/G), Alanine (Ala/A);
2) Isoleucine (Ile/I), Leucine (Leu/L), Methionine (Met/M), Valine (Val/V);
3) Phenylalanine (Phe/F), Tyrosine (Tyr/Y), Tryptophan (Trp/W);
4) Serine (Ser/S), Threonine (Thr/T), Cysteine (Cys/C);
5) Asparagine (Asn/N), Glutamine (Gln/Q);
6) Aspartic acid (Asp/D), Glutamic acid (Glu/E); and
7) Arginine (Arg/R), Lysine (Lys/K), Histidine (His/H).

In further embodiments, the following groups each contain natural amino acids that are conservative substitutions for one another:

1) non-polar: Ala, Val, Leu, Ile, Met, Pro (proline/P), Phe, Trp;
2) hydrophobic: Val, Leu, Ile, Phe, Tyr, Trp;
3) aliphatic: Ala, Val, Leu, Ile;
4) aromatic: Phe, Tyr, Trp, His;
5) uncharged polar or hydrophilic: Gly, Ala, Pro, Ser, Thr, Cys, Asn, Gln, Tyr (tyrosine may be regarded as a hydrophobic amino acid with a polar side group);
6) aliphatic hydroxyl- or sulfhydryl-containing: Ser, Thr, Cys;
7) amide-containing: Asn, Gln;
8) acidic: Asp, Glu;
9) basic: Lys, Arg, His; and
10) small: Gly, Ala, Ser, Cys.

In other embodiments, amino acids may be grouped as set out below:

1) hydrophobic: Val, Leu, Ile, Met, Phe, Trp, Tyr;
2) aromatic: Phe, Tyr, Trp, His;
3) neutral hydrophilic: Gly, Ala, Pro, Ser, Thr, Cys, Asn, Gln;
4) acidic: Asp, Glu;
5) basic: Lys, Arg, His; and
6) residues that influence backbone orientation: Pro, Gly.

A polypeptide having one or more modifications relative to a parent polypeptide may be called an "analog", "derivative" or "variant" of the parent polypeptide as appropriate.

The disclosure encompasses pharmaceutically acceptable salts of polypeptides, including those with a positive net charge, those with a negative net charge, and those with no net charge.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" excipient or carrier of a pharmaceutical composition is also compatible with the other ingredients of the composition.

The term "stringent hybridization conditions" refers to hybridizing in 50% formamide at 5×SSC at a temperature of 42° C. and washing the filters in 0.2×SSC at 60° C. (1×SSC is 0.15M NaCl, 0.015M sodium citrate.) Stringent hybridization conditions also encompasses low ionic strength and high temperature for washing, for example 0.015 M sodium chloride/0.0015 M sodium citrate/0.1% sodium dodecyl sulfate at 50° C.; hybridization with a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The term "subject" refers to an animal, including but not limited to a mammal, such as a primate (e.g., a human, a chimpanzee or a monkey), a rodent (e.g., a rat, a mouse, a guinea pig, a gerbil or a hamster), a lagomorph (e.g., a rabbit), a swine (e.g., a pig), an equine (e.g., a horse), a canine (e.g., a dog) or a feline (e.g., a cat).

The term "substantially homologous" or "substantially identical" in the context of two polypeptides or polynucleotides refers to two or more sequences or subsequences that have at least about 50%, 60%, 65%, 70%, 75%, 80%, 85%, 90%, 95%, 96%, 97%, 98% or 99% amino acid or nucleic acid residue identity, when compared and aligned for maximum correspondence, as measured using a sequence comparison algorithm or by visual inspection. The terms "substantially homologous" or "substantially identical" can mean at least about 70% amino acid or nucleic acid residue identity. The term "substantially homologous" or "substantially identical" can mean at least about 85% amino acid or nucleic acid residue identity. The substantial homology or identity can exist over a region of the sequences that is at least about 20, 30, 40, 50, 100, 150 or 200 residues in length. The sequences can be substantially homologous or identical over the entire length of either or both comparison biopolymers.

Optimal alignment of sequences for comparison can be conducted, e.g., by the local homology algorithm of Smith and Waterman, *Adv. Appl. Math.*, 2:482 (1981); by the homology alignment algorithm of Needleman and Wunsch, *J. Mol. Biol.*, 48:443 (1970); by the search for similarity method of Pearson and Lipman, *Proc. Natl. Acad. Sci. USA*, 85:2444 (1988); by computerized implementations of these algorithms (e.g., GAP, BESTFIT, FASTA, and TFASTA in the Wisconsin Genetics Software Package, Genetics Computer Group, Madison, Wis.); or by visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle, *J. Mol. Evol.*, 35:351-360 (1987). The method used is similar to the method described by Higgins and Sharp, *CABIOS*, 5:151-153 (1989). The program can align up to about 300 sequences, each having a maximum length of about 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (see, e.g., Thompson et al., *Nucleic Acids Research*, 22:4673-4680 [1994]).

Another example of an algorithm that is suitable for determining percent sequence identity and sequence similarity is the BLAST algorithm, which is described in Altschul et al., *J. Mol. Biol.*, 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults, e.g., a wordlength (W) of 11, an expectation (E) of 10, M=5, N=−4, and a comparison of both strands. For amino acid sequences, the BLASTP program uses as defaults, e.g., a wordlength (W) of 3, an expectation (E) of 10, and the BLOSUM62 scoring matrix (see Henikoff and Henikoff, *Proc. Natl. Acad. Sci. USA*, 89:10915 [1989]).

In addition to calculating percent sequence identity, the BLAST algorithm also performs a statistical analysis of the similarity between two sequences (see, e.g., Karlin and Altschul, *Proc. Natl. Acad. Sci. USA*, 90:5873-5787 [1993]). One measure of similarity provided by the BLAST algorithm is the smallest sum probability [P(N)], which provides an indication of the probability by which a match between two nucleotide or amino acid sequences would occur by chance. In certain embodiments, a polynucleotide is considered similar to a reference sequence if the smallest sum probability in a comparison of the test polynucleotide to the reference polynucleotide is less than about 0.1, 0.01 or 0.001.

A polypeptide can be substantially homologous or identical to a second polypeptide if the two polypeptides differ only by conservative amino acid substitutions. Two nucleic acid sequences can be substantially homologous or identical if the two polynucleotides hybridize to each other under stringent conditions, or under highly stringent conditions, as described herein.

The term "therapeutically effective amount" refers to an amount of a compound that, when administered to a subject, is sufficient to prevent, reduce the risk of developing, delay the onset of, slow the progression or cause regression of the medical condition being treated, or to alleviate to some extent the medical condition or one or more symptoms or complications of that condition. The term "therapeutically effective amount" also refers to an amount of a compound that is sufficient to elicit the biological or medical response of a cell, tissue, organ, system, animal or human which is sought by a researcher, veterinarian, medical doctor or clinician.

The terms "treat", "treating" and "treatment" include alleviating, ameliorating or abrogating a medical condition or one or more symptoms or complications associated with the condition, and alleviating, ameliorating or eradicating one or more causes of the condition. Reference to "treatment" of a medical condition includes prevention of the condition. The terms "prevent", "preventing" and "prevention" include precluding, reducing the risk of developing and delaying the onset of a medical condition or one or more symptoms or complications associated with the condition.

Anti-CD79 Antibodies

Antibodies described herein have specificity for CD79 and include all the forms described above. The antibody can be engineered for use in a particular organism. The organism can be a human, canine, or a commercially valuable livestock, such as, for example, pigs, horses, dogs, cats, chickens, or other birds. Such engineering of the antibody includes, for example, CDR splicing, humanization, humaneering, chimerization, or isolating human (or other organism) antibodies using any of the repertoire technologies or monoclonal technologies known in the art.

An anti-CD79 antibody can include a heavy chain variable region selected from SEQ ID NOs: 9-17, 24-27, and 32-41, and a light chain variable region selected from SEQ ID NOs: 18-23, 28-31, and 42-56. For Example, a heavy chain with a variable region of SEQ ID NO: 9 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 71, 72, 75, 76, or 77. A heavy chain with a variable region of SEQ ID NO: 10 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 11 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 12 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 13 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 14 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 15 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 16 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 17 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 24 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 25 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 26 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 27 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 28 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 33 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 34 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 35 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 36 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 37 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 38 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 39 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 40 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 41 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 71 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 72 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 75 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 76 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74. A heavy chain with a variable region of SEQ ID NO: 77 can be combined with light chain having a variably region of SEQ ID NOs; 18, 19, 20, 21, 22, 23, 28, 29, 30, 31, 42, 43, 44, 45, 46, 47, 48, 49, 50, 51, 52, 53, 54, 55, 56, 73, or 74.

An anti-CD79 antibody can also include a heavy chain variable region that has 99%, 95%, 90%, 80% or 70% sequence identity with one of SEQ ID NOs: 9-17, 24-27, 32-41, 71, 72, and 75-77, and a light chain variable selected from SEQ ID NOs: 18-23, 28-31, 42-56, and 73-74. An anti-CD79 antibody can also include a heavy chain variable region that has 99%, 95%, 90%, 80% or 70% sequence identity with one of SEQ ID NOs: 9-17, 24-28, and 33-43, and a light chain variable region that has 99%, 95%, 90%, 80% or 70% sequence identity with one of SEQ ID NOs: 18-23, 28-31, 42-56, and 73-74. An anti-CD79 antibody can also include a heavy chain variable region selected from SEQ ID NOs: 9-17, 24-27, 32-41, 71, 72, and 75-77, and a light chain variable region that has 99%, 95%, 90%, 80% or 70% sequence identity with one of SEQ ID NOs: 18-23, 28-31, 42-56, and 73-74. An anti-CD79 antibody can bind to CD79 with an affinity of 2.0-5.1 nM, or 45 nM to 300 nM, or 2.0 to 300 nM. An anti-CD79 antibody can bind with an affinity of at least 300 nM, or at least 140 nM, or at least 100 nM, or at least 5.1 nm, at least 3.8 nM, or at least 2.4 nM.

Affinity maturation can be used with an antibody disclosed herein to obtain an anti-CD79 antibody of a desired affinity. When an anti-CD79 antibody is obtained from an animal (e.g., a transgenic animal carrying a human antibody repertoire), the antibodies made in the transgenic animal can undergo affinity maturation. Alternatively, antibodies from a transgenic animal, or from other technologies (such as a display technology) can be affinity matured using chain shuffling approaches and/or mutation of the nucleic acids encoding VH and VL followed by screening and/or selecting for antibodies with greater affinity.

The most widely used methods for minimizing the immunogenicity of non-human antibodies while retaining specificity and affinity involve grafting the CDRs of the non-human antibody onto human frameworks typically selected for their structural homology to the non-human framework (Jones et al., 1986, Nature 321:522-5; U.S. Pat. No. 5,225, 539, both of which are hereby incorporated by reference in their entirety). The inclusion of some non-human residues at key positions in the framework can improve the affinity of the CDR grafted antibody (Bajorath et al., 1995, J Biol Chem 270:22081-4; Martin et al., 1991, Methods Enzymol. 203:121-53; Al-Lazikani, 1997, J Mol Biol 273:927-48, all of which are hereby incorporated by reference in their entirety). Exemplary methods for humanization of antibodies by CDR grafting are disclosed, for example, in U.S. Pat. No. 6,180,370, which is hereby incorporated by reference in its entirety.

Improvements to the traditional CDR-grafting approaches use various hybrid selection approaches, in which portions of the non-human antibody have been combined with libraries of complementary human antibody sequences in successive rounds of selection for antigen binding, in the course of which most of the non-human sequences are gradually replaced with human sequences. For example, in the chain-shuffling technique (Marks, et al., 1992, Biotechnology 10:779-83, which is hereby incorporated by reference in its entirety) one chain of the non-human antibody is combined with a naive human repertoire of the other chain on the rationale that the affinity of the non-human chain will be sufficient to constrain the selection of a human partner to the same epitope on the antigen. Selected human partners are then used to guide selection of human counterparts for the remaining non-human chains.

Other methodologies include chain replacement techniques where the non-human CDR3s were retained and only the remainder of the V-regions, including the frameworks and CDRs 1 and 2, were individually replaced in steps performed sequentially (e.g., U.S. Patent Application No. 20030166871; Rader, et al., Proc Natl Acad Sci USA 95:8910-15, 1998; Steinberger, et al., J. Biol. Chem. 275: 36073-36078, 2000; Rader, et al., J. Biol. Chem. 275:13668-13676, 2000, all of which are hereby incorporated by reference in their entirety).

These technologies can be used to make antibodies suitable for use in non-human subjects by engineering the CDRs into framework regions of the subject species using analogous approaches to the CDR grafting methods used for make antibodies for use in humans.

Anti-CD79 antibodies can be made using a starting anti-CD79 antibody and grafting portions of the variable region (e.g., the CDRs) of the starting anti-CD79 antibody into a desired variable domain framework. The mouse variable regions were:

```
(Heavy Chain variable region, SEQ ID NO: 1)
QVQLQQSGPELVKPGASVKISCKASGYAFSYSWMNWVKQRPGKGLEWIGR

IYPENGDTNYNGKFKGKVTLTADKSSSTAYMQLSSLTSEDSAVYFCARWV

YGYPHFDYWGQGTTLTVSS (Light Chain variable region, SEQ ID NO: 2)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCWQGTHFP

FTFGSGTKLEIK
```

Anti-CD79, humanized antibodies were made, for example, using the CDRs:

```
V_H CDR1:
                                          (SEQ ID NO: 3)
YSWMN

V_H CDR2:
                                          (SEQ ID NO: 4)
RIYPENGDTNYNGKFKG

V_H CDR3:
                                          (SEQ ID NO: 5)
WVYGYPHFDY

V_L CDR1:
                                          (SEQ ID NO: 6)
KSSQSLLDSDGKTYLN

V_L CDR2:
                                          (SEQ ID NO: 7)
LVSKLDS

V_L CDR3:
                                          (SEQ ID NO: 8)
WQGTHFPFT
```

The three VH CDRs were placed into the framework sequences of a human variable region for a heavy chain to produce the VH chain:

```
                                          (SEQ ID NO: 9)
QVQLVQSGAEVKKPGASVKVSCKASGYAFSYSWMNWVRQAPGQGLEWMGR

IYPENGDTNYNGKFKGRVTMTRDTSISTAYMELSRLRSDDTAVYYCARWV

YGYPHFDYWGQGTLVTVSS
```

This VH was designated H1. Substitutions were introduced into the framework regions of SEQ ID NO: 9 to make two additional VH chains:

```
                                          (SEQ ID NO: 10)
QVQLVQSGAEVKKPGASVKVSCKASGYAFSYSWMNWVRQAPGQGLEWMGR

IYPENGDTNYNGKFKGRVTMTADTSISTAYMELSRLRSDDTAVYYCARWV

YGYPHFDYWGQGTLVTVSS
```

SEQ ID NO: 10 was designated H2.

```
                                          (SEQ ID NO: 11)
QVQLVQSGAEVKKPGASVKVSCKASGYAFSYSWMNWVRQAPGQGLEWIGR

IYPENGDTNYNGKFKGRVTLTADKSISTAYMELSRLRSDDTAVYYCARWV

YGYPHFDYWGQGTLVTVSS
```

SEQ ID NO: 11 was designated H3. Additional changes can be introduced to SEQ ID NO: 9 in the framework regions and CDR2 to increase affinity and/or stabilize the antibody against, for example, oxidation, deamination, and/or protease cleavage. Examples of these heavy chain sequences are:

```
                                          (SEQ ID NO: 12)
QVQLVQSGAEVKKPGASVKVSCKASGYAFSYSWMNWVRQAPGQGLEWMGR

IYPENGDTNYAGKFKGRVTMTRDTSISTAYMELSRLRSDDTAVYYCARWV

YGYPHFDYWGQGTLVTVSS
```

SEQ ID NO: 12 is designated H4.

(SEQ ID NO: 13)
QVQLVQSGAEVKKPGASVKVSCKASGYAFSYSWMNWVRQAPGQGLEWMGR

IYPENGDTNYAGKFKGRVTMTADTSISTAYMELSRLRSDDTAVYYCARWV

YGYPHFDYWGQGTLVTVSS

SEQ ID NO: 13 is designated H5.

(SEQ ID NO: 14)
QVQLVQSGAEVKKPGASVKVSCKASGYAFSYSWMNWVRQAPGQGLEWIGR

IYPENGDTNYAGKFKGRVTLTADKSISTAYMELSRLRSDDTAVYYCARWV

YGYPHFDYWGQGTLVTVSS

SEQ ID NO: 14 is designated H6.

(SEQ ID NO: 15)
QVQLVQSGAEVKKPGASVKVSCKASGYAFSYSWMNWVRQAPGQGLEWMGR

IYPESGDTNYAGKFKGRVTMTRDTSISTAYMELSRLRSDDTAVYYCARWV

YGYPHFDYWGQGTLVTVSS

SEQ ID NO: 15 is designated H7.

(SEQ ID NO: 16)
QVQLVQSGAEVKKPGASVKVSCKASGYAFSYSWMNWVRQAPGQGLEWMGR

IYPESGDTNYAGKFKGRVTMTADTSISTAYMELSRLRSDDTAVYYCARWV

YGYPHFDYWGQGTLVTVSS

SEQ ID NO: 16 is designated H8.

(SEQ ID NO: 17)
QVQLVQSGAEVKKPGASVKVSCKASGYAFSYSWMNWVRQAPGQGLEWIGR

IYPESGDTNYAGKFKGRVTLTADKSISTAYMELSRLRSDDTAVYYCARWV

YGYPHFDYWGQGTLVTVSS

SEQ ID NO: 17 is designated H9.

The three VL CDRs were placed into the framework sequences for a human variable region from a light chain to produce the VL chain:

(SEQ ID NO: 18)
DVVMTQSPLSLPVTLGQPASISCKSSQSLLDSDGKTYLNWFQQRPGQSPR

RLIYLVSKLDSGVPDRFSGSGSGTDFTLKISRVEAEDVGVYYCWQGTHFP

FTFGGGTKVEIK

SEQ ID NO: 18 was designated L1. Substitutions were introduced into the framework regions of SEQ ID NO: 18 to make additional VL chains:

(SEQ ID NO: 19)
DVVMTQSPLSLPVTLGQPASISCKSSQSLLDSDGKTYLNWLQQRPGQSPR

RLIYLVSKLDSGVPDRFSGSGSGTDFTLKISRVEAEDVGVYYCWQGTHFP

FTFGGGTKVEIK

SEQ ID NO: 19 was designated L2.

(SEQ ID NO: 20)
DVVMTQSPLSLPVTLGQPASISCKSSQSLLDSDGKTYLNWLQQRPGQSPK

RLIYLVSKLDSGVPDRFSGSGSGTDFTLKISRVEAEDVGVYYCWQGTHFP

FTFGGGTKVEIK

SEQ ID NO: 20 was designated L3. Additional changes can be introduced into SEQ ID NO: 18 in the framework regions and CDR1 to increase affinity and/or stabilize the antibody against, for example, oxidation, deamination, and/or protease cleavage. Examples of these light chain sequences are:

(SEQ ID NO: 21)
DVVMTQSPLSLPVTLGQPASISCKSSQSLLDSSGKTYLNWFQQRPGQSPR

RLIYLVSKLDSGVPDRFSGSGSGTDFTLKISRVEAEDVGVYYCWQGTHFP

FTFGGGTKVEIK

SEQ ID NO: 21 was designated L4.

(SEQ ID NO: 22)
DVVMTQSPLSLPVTLGQPASISCKSSQSLLDSSGKTYLNWLQQRPGQSPR

RLIYLVSKLDSGVPDRFSGSGSGTDFTLKISRVEAEDVGVYYCWQGTHFP

FTFGGGTKVEIK

SEQ ID NO: 22 was designated L5.

(SEQ ID NO: 23)
DVVMTQSPLSLPVTLGQPASISCKSSQSLLDSSGKTYLNWLQQRPGQSPK

RLIYLVSKLDSGVPDRFSGSGSGTDFTLKISRVEAEDVGVYYCWQGTHFP

FTFGGGTKVEIK

SEQ ID NO: 23 was designated L6.

Three VH chains (H1-H3) were combinatorially combined with the three VL chains (L1-L3) and each antibody was recombinantly expressed and isolated. The H1-H3 and L1-L3 antibody chains have related framework regions that differ at few positions which could improve affinity. These candidates were tested for affinity to CD79. The candidates bound to CD79 with $K_d$s ranging from 45 nM to 300 nM. H1L2 (LB495/PRI47, SEQ ID NOs: 9 and 19) was chosen from these results.

The disclosure encompasses pharmaceutically acceptable salts of anti-CD79 antibodies, including those with a positive net charge, those with a negative net charge, and those with no net charge, and including without limitation salts of anti-CD79 antibodies including fragments thereof as compounds, in pharmaceutical compositions, in their therapeutic and diagnostic uses, and in their production.

Affinity Maturation

The humanized antibody H1L2 (SEQ ID NOs: 9 and 19) was affinity matured. Four phage display libraries were made, two from the heavy chain H1 (LB495) and two from the light chain L2 (PRI47). Saturation mutagenesis was performed on the CDR3 of the heavy (H1) and light (L2) chains and the mutagenized heavy chains were combined with L2, and the mutagenized light chains were combined with H1. Error prone PCR was used to randomly mutagenize the heavy (H1) and light (L2) chains and the mutagenized heavy chains were combined with L2, and the mutagenized light chains were combined with H1. These four libraries were produced in a phage display format for further screening.

Each library was panned against CD79 in a competitive binding which included humanized antibody H1L2. Clones from the libraries were selected in a competitive panning in which humanized H1L2 antibody was added and to attach to CD79 on a substrate the clones had to compete with the humanized H1L2 antibody. Thirty seven (37) clones were obtained from competitive pannings of the four libraries (five (5) from the CDR3 heavy chain library, four (4) from the CDR3 light chain library, eleven (11) from the heavy chain library, and 17 from the light chain library). The sequences of these 5 clones from the CDR3 heavy chain library were:

(SEQ ID NO: 24)
QVQLVQSGAEVKKPGASVKVSCKASGYAFSYSWMNWVRQAPGQGLEWMGR
IYPENGDTNYNGKFKGRVTMTRDTSISTAYMELSRLRSDDTAVYYCARPV
YGYPHFDYWGQGTLVTVSS

SEQ ID NO: 24 was designated LB509-A7.

(SEQ ID NO: 25)
QVQLVQSGAEVKKPGASVKVSCKASGYAFSYSWMNWVRQAPGQGLEWMGR
IYPENGDTNYNGKFKGRVTMTRDTSISTAYMELSRLRSDDTAVYYCARWV
YGLPHFDYWGQGTLVTVSS

SEQ ID NO: 25 was designated LB509-C2.

(SEQ ID NO: 26)
QVQLVQSGAEVKKPGASVKVSCKASGYAFSYSWMNWVRQAPGQGLEWMGR
IYPENGDTNYNGKFKGRVTMTRDTSISTAYMELSRLRSDDTAVYYCARWV
WGYPHFDYWGQGTLVTVSS

SEQ ID NO: 26 was designated LB509-C10.

(SEQ ID NO: 27)
QVQLVQSGAEVKKPGASVKVSCKASGYAFSYSWMNWVRQAPGQGLEWMGR
IYPENGDTNYNGKFKGRVTMTRDTSISTAYMELSRLRSDDTAVYYCARWV
YGYPHLDYWGQGTLVTVSS

SEQ ID NO: 27 was designated LB509-G2.

(SEQ ID NO: 71)
QVQLVQSGAEVKKPGASVKVSCKASGYAFSYSWMNWVRQAPGQGLEWMGR
IYPENGDTNYNGKFKGRVTMTRDTSISTAYMELSRLRSDDTAVYYCARWV
YGYPHLDYWGQGTLVTVSS

SEQ ID NO: 71 was also designated LB509-H1.

The sequences of the 4 clones from the CDR3 light chain library were:

(SEQ ID NO: 28)
DVVMTQSPLSLPVTLGQPASISCKSSQSLLDSDGKTYLNWLQQRPGQSPR
RLIYLVSKLDSGVPDRFSGSGSGTDFTLKISRVEAEDVGVYYCWQGTHIP
FTFGGGTKVEIK

SEQ ID NO: 28 was designated LB511-A9.

(SEQ ID NO: 29)
DVVMTQSPLSLPVTLGQPASISCKSSQSLLDSDGKTYLNWLQQRPGQSPR
RLIYLVSKLDSGVPDRFSGSGSGTDFTLKISRVEAEDVGVYYCWQGTHVP
FTFGGGTKVEIK

SEQ ID NO: 29 was designated LB511-B6.

(SEQ ID NO: 30)
DVVMTQSPLSLPVTLGQPASISCKSSQSLLDSDGKTYLNWLQQRPGQSPR
RLIYLVSKLDSGVPDRFSGSGSGTDFTLKISRVEAEDVGVYYCWQGTHLP
FTFGGGTKVEIK

SEQ ID NO: 30 was designated LB511-F6.

(SEQ ID NO: 31)
DVVMTQSPLSLPVTLGQPASISCKSSQSLLDSDGKTYLNWLQQRPGQSPR
RLIYLVSKLDSGVPDRFSGSGSGTDFTLKISRVEAEDVGVYYCWQGTHRP
FTFGGGTKVEIK

SEQ ID NO: 31 was designated LB511-F11.

The sequences of the 11 clones from the heavy chain library were:

(SEQ ID NO: 32)
QVQLVQSGAEVKKPGASVKVSCKASGYAFSYSWINWVRQAPGQGLEWMGR
IYPENGDTNYNGKFKGRVTMTRDTSISTAYMELSRLRSDDTAVYYCARWV
YGYPHFDYWGQGTLVTVSS

SEQ ID NO: 32 was designated LB510-B5.

(SEQ ID NO: 33)
QVQLVQSGAEVKKPGASVKVSCKASGYAFGYSWMNWVRQAPGQGLEWMGR
IYPENGDTNYNGKFKGRVTMTRDTSISTAYMELSRLRSDDTAVYYCARWV
YGYPHFDYWGQGTLVTVSS

SEQ ID NO: 33 was designated LB510-C7.

(SEQ ID NO: 34)
QVQLVQSGAEVKKPGASVKVSCKASGYAFSYSWMNWVRQAPGQGLEWMGR
IYPENGDTNYNGKFKGRVTMTRDTSISTAYMELSRLRPDDTAVYYCARWV
YGYPHFDYWGQGTLVTVSS

SEQ ID NO: 34 was designated LB510-C8.

(SEQ ID NO: 35)
QVQLVQSGAEVKKPGASVKVSCKASGYAFNYSWMNWVRQVPGQGLEWMGR
IYPENGDTNYNGKFKGRVTMTRDTSISTAYMELSRLRSDDTAVYYCARWV
YGYPHFDYWGQGTLVTVSS

SEQ ID NO: 35 was designated LB510-F10.

(SEQ ID NO: 36)
QVQLVQSGAEVKKPGASVKVSCKASGYAFSYSWMNWVRQAPGQGLEWMGR

IYPENGDTNYNGKFKGRVTMTRDTSINTAYMELSRLRSDDTAVYYCARWV

YGYPHFDYWGQGTLVTVSS

SEQ ID NO: 36 was designated LB510-G4.

(SEQ ID NO: 37)
QVQLVQSGAEVKKPGASVKVSCKASGYAFSYSWVNWVRQAPGQGLEWMGR

IYPENGDTNYNGKFKGRVTMTRDTSISTAYMELSRLRSDDTAVYYCARWV

YGYPHFDYWGQGTLVTVSS

SEQ ID NO: 37 was designated LB510-G5.

(SEQ ID NO: 38)
QVQLVQSGAEVKKPGASVKVSCKASGYAFSYSWMNWVRQAPGQGLEWMGR

IYPENGDTNYNGKFKGRVTMTRDTSISTAYMELSGLRSDDTAVYYCARWV

YGYPHFDYWGQGTLVTVSS

SEQ ID NO: 38 was designated LB510-G6.

(SEQ ID NO: 39)
QVQLVQSGAEVKKPGASVKVSCKASGYAFSYSWMNWVRQAPGQGLEWMGR

IYPENGDTNYNGKFKGRVTMTRDTSISTAYMELSRLRSDDTAVYYCARWV

YGYPHLDYWGQGTLVTVSS

SEQ ID NO: 39 was designated LB510-G7.

(SEQ ID NO: 72)
QVQLVQSGAEVKKPGASVKVSCKASGYAFNYSWVNWVRQAPGQGFEWMGR

IYPENGDTNYNGKFKGRVTMTRDTSISTAYMELSRLRSDDTAVYYCARWV

YGYPHFDYWGQGTLVTVSS

SEQ ID NO: 72 was also designated LB510-H4.

(SEQ ID NO: 40)
QVQLVQSGAEVKKPGASVKVSCKASGYAFRYSWMNWVRQAPGQGLEWMGR

IYPENGGTNYNGKFKGRVTMTMDTSISTAYMELSRLRSDDTAVYYCARWV

YGYPHFDYWGQGTLVTVSS

SEQ ID NO: 40 was designated LB510-H7.

(SEQ ID NO: 41)
QVQLVQSGAEVKKPGASVKVSCKASGYAFSYSWMNWVRQAPGQGLEWMGR

IYPENGDTNYNGKFRGRVTMTRDTSISTAYMELSRLRSDDTAVYYCARWV

YGYPHFDYWGQGTLVTVSS

SEQ ID NO: 41 was designated LB510-H11.

The sequences of the 17 clones from the light chain library were:

(SEQ ID NO: 42)
DVVMTQSPLSLPVTLGLPASISCKSSQSLLDSDGKTYLNWLQQRPGQSPR

RLIYLVSKLDSGVPDRFSGSGSGTDFTLKISRVEAEDVGVYYCWQGTHFP

FTFGGGTKVEIK

SEQ ID NO: 42 was designated LB512-A7.

(SEQ ID NO: 43)
DVVMTQSPLSLPVTLGQPASISCKSSKSLLDSDGKTYLNWLQQRPGQSPR

RLIYLVSKLDSGVPDRFSGSGSGTDFTLKISRVEAEDVGVYYCWQGTHFP

FTFGGGTKVEIK

SEQ ID NO: 43 was designated LB512-A10.

(SEQ ID NO: 44)
DVVMTQSPLSLPVTLGQPASISCKSSQSLLDSDGKTYLNWLQQRPGQSPR

RIIYLVSKLDSGVPDRFSGSGSGTDFTLKISRVEAEDVGVYYCWQGTHFP

FTFGGGTKVEIK

SEQ ID NO: 44 was designated LB512-B8.

(SEQ ID NO: 45)
DVVMTQSPLSLPVTLGQPASISCKSSQSLLDSDGKTYLNWLQQRPGQSPR

RLIYLVSKLDSGVPDRFSGSGSGTDFTLKISRVEADDVGVYYCWQGTHLP

FTFGGGTKVEIK

SEQ ID NO: 45 was designated LB512-B10.

(SEQ ID NO: 46)
DVVMTQSPLSLPVTLGQPASISCKSSQSLLDSDGKTYLNWLQQRPGQSPR

RLIYLVSKLDSGVPDRFSGSGSGTDFTLKISRVEAEDVGFYYCWQGTHLP

FTFGGGTKVEIK

SEQ ID NO: 46 was designated LB512-C2.

(SEQ ID NO: 47)
DVVMTQSPLSLPVTLGQTASISCKSSQSLLDSDGKTYLNWLQQRPGQSPR

RLIYLVSKLDSGVPDRFSGSGSGTDFTLKISRVEAEDVGVYYCWQGTHLP

FTFGGGTKVEIK

SEQ ID NO: 47 was designated LB512-E2.

(SEQ ID NO: 48)
DVVMTQSPLSLPVTLGRPASISCKSSQSLLDSGGKTYLNWLQQRPGQSPR

RLIYLVSKLDSGVPDRFSGSGSGTDFTLKISRVEAEDVGVYYCWQGTHFP

FTFGGGTKVEIK

SEQ ID NO: 48 was designated LB512-E5.

(SEQ ID NO: 49)
DVVMTQSPLSLPVTLGQPASISCKSSRSLLDSDGKTYLNWLQQRPGQSPR
RLIYLVSKLDSGVPDRFSGSGSGTDFTLKISRVEAEDVGVYYCWQGTHFP
FTFGGGTKVEIK

SEQ ID NO: 49 was designated LB512-E8.

(SEQ ID NO: 50)
DVVMTQSPLSLPVTLGLPASISCKSSQSLLDTDGKTYLNWLQQRPGQSPR
RLIYLVSKLDSGVPDRFIGSGSGTDFTLKISRVEAEDVGVYYCWQGTHFP
FTFGGGTKVEIK

SEQ ID NO: 50 was designated LB512-E10.

(SEQ ID NO: 73)
DVVMTQSPLSLPVTLGQPASISCKSSQSLLDSDGKTYLNWLQQRPGQSPR
RLIYLVSKLDSGVPDRFSGSGSGTDFTLKISRVEAEDVGVYYCWQGTHLP
FTFGGGTKVEIK

SEQ ID NO: 73 was also designated LB512-F7.

(SEQ ID NO: 51)
DVVMTQSPLSLPVTLGQPASISCKSSQSLLDSDGKTYLNWLQQRPGQPPR
RLIYLVSKLDSGVPDRFSGSGSGTDFTLKISRVEAEDVGVYYCWQGTHFP
FTFGGGTKVEIK

SEQ ID NO: 51 was designated LB512-F11.

(SEQ ID NO: 52)
DVVMTQSPLSLPVTLGQPASITCKSSQSLLDSDGKTYLNWLQQRPGQSPR
RLIYLVSKPDSGVPDRFSGSGSGTDFTLKISRVEAEDVGVYYCWQGTHFP
FTFGGGTKVEIK

SEQ ID NO: 52 was designated LB512-G2.

(SEQ ID NO: 74)
DVVMTQSPLSLPVTLGQPASISCKSSQSLLDSDGKTYLNWLQQRPGQSPR
RLIYLVSKLDSGVPDRFSGSGSGTDFTLKISRVEAEDVGVYYCWQGTHLP
FTFGGGTKVEIK

SEQ ID NO: 74 was also designated LB512-G5.

(SEQ ID NO: 53)
DVVMTQSPPSLPVTLGQPASISCKSSQSLLDSDGKTYLNWLQQRPGQSPR
RLIYLVSKLDSGVPDRFSGSGSGTDFTLKISRVEAEDVGVYYCWQGTHVP
FTFGGGTKVEIK

SEQ ID NO: 53 was designated LB512-H5.

(SEQ ID NO: 54)
DVVMTQSPLSLPVTLGQTASISCKSSQSLLDRDGKTYLNWLQQRPGQSPR
RIIYLVSKLDSGVPDRFSGSGSGTDFTLKISRVEAEDVGVYYCWQGTHFP
FTFGGGTKVEIK

SEQ ID NO: 54 was designated LB512-H7.

(SEQ ID NO: 55)
DVVMTQSPLSMPVTLGLPASISCKSSQSLLDSHGKTYLNWLQQRPGQSPR
RLIYLVSKLDSGVPDRFSGSGSGTDFTLKISRVEAEDVGVYYCWQGTHFP
FTFGGGTKVEIK

SEQ ID NO: 55 was designated LB512-H8.

(SEQ ID NO: 56)
DVVMTQSPLSLPVTLGLPASISCKSSQSLLDSDGKTYLNWLQQRPGQSPR
RLIYLVSKLDSGVPDRFSGSGSGTDFTLKISRVEAEDVGVYYCWQGTHIP
FTFSGGTKVEIK

SEQ ID NO: 56 was designated LB512-H11.

These 37 clones were screened in a competition ELISA. Clones that had better binding than the patent antibody (H1L2) were picked. Nine clones were obtained from the competition ELISA as having better affinity. Two from the heavy chain CDR3 library (LB509-C2, SEQ ID NO: 25; and LB509-G2, SEQ ID NO: 27), four from the light chain CDR3 library (LB511-A9, SEQ ID NO: 28; LB511-B6, SEQ ID NO: 29; LB511-F6, SEQ ID NO: 30; LB511-F11, SEQ ID NO: 31), two from the heavy chain library (LB510-C7, SEQ ID NO: 33; LB510-G5, SEQ ID NO: 37), and one from the light chain library (A7, SEQ ID NO: 42). These clones were subjected to a confirmatory dilution ELISA, and five clones that exhibited better binding were selected (heavy chain CDR clone LB509-C2, SEQ ID NO: 25; light chain CDR clones LB51-A9, SEQ ID NO: 28, LB511-B6, SEQ ID NO: 29, LB511-F6, SEQ ID NO: 30, and LB511-F11, SEQ ID NO: 31). Heavy chain CDR clone C2 had a Y to L change in CDR3, and Light chain clones A9, B6, F6, and F11 had an amino acid change at the same position changing an F to L, V, I, or R in CDR3. Two heavy chains with the H1 sequence (SEQ ID NO: 10), designated LB495, or the Y to L change (SEQ ID NO: 25), designated LB517, were made, and five light chains with the L2 sequence (SEQ ID NO: 19), designated PRI47, or the F to I in CDR3 of L2 (SEQ ID NO: 28), designated LB518, F to L in CDR3 of L2 (SEQ ID NO: 30), designated LB519, F to R in CDR3 of L2 (SEQ ID NO: 31), designated LB520, or F to V in CDR3 of L2 (SEQ ID NO: 29), designated LB521, changes were made. The two heavy chains were each combinatorially combined individually with the five light chains, and these antibodies were tested for binding kinetics.

All the affinity matured antibody combinations had higher affinity for binding to the CD79 than the parent antibody H1L2. The parent antibody has a $K_d$ of 5.1 nM for CD79, and the affinity matured antibodies had $K_d$ of 3.6 nM to 2.0 nM for CD79.

Anti-CD79 Antibody Modifications

An anti-CD79 antibody can include a moiety that extends a half-life ($T_{1/2}$) or/and the duration of action of the antibody. The moiety can extend the circulation $T_{1/2}$, blood $T_{1/2}$, plasma $T_{1/2}$, serum $T_{1/2}$, terminal $T_{1/2}$, biological $T_{1/2}$, elimination $T_{1/2}$ or functional $T_{1/2}$, or any combination thereof, of the antibody.

An anti-CD79 antibody may be modified by a single moiety. Alternatively, an anti-CD79 antibody may be modified by two or more substantially similar or identical moieties or two or more moieties of the same type. An anti-CD79 antibody may include two or more moieties of different types, or two or more different types of moieties. Two or more anti-CD79 antibodies can also be attached to one moiety. The attachment between the anti-CD79 antibody and the moiety can be covalent or noncovalent.

A polypeptide moiety can be recombinantly fused to the N-terminus or the C-terminus of the heavy chain or the light chain of an anti-CD79 antibody, optionally via a linker. The linker may contain about 4-30 amino acid residues. The linker may contain from about 6 or 8 amino acid residues to about 20 amino acid residues, or from about 6 or 8 amino acid residues to about 15 amino acid residues.

A protracting moiety can be human serum albumin (HSA) or a portion thereof (e.g., domain III) that binds to the neonatal Fc receptor (FcRn). The HSA or FcRn-binding portion thereof can optionally have one or more mutations that confer a beneficial property or effect. In some embodiments, the HSA or FcRn-binding portion thereof has one or more mutations that enhance pH-dependent HSA binding to FcRn or/and increase HSA half-life, such as K573P or/and E505G/V547A. A protracting moiety can be an unstructured polypeptide.

A protracting moiety can be a carboxy-terminal peptide (CTP) derived from the β-subunit of human chorionic gonadotropin (hCG). In the human body, the fourth, fifth, seventh and eight serine residues of the 34-aa CTP of hCG-β typically are attached to O-glycans terminating with a sialic acid residue.

A protracting moiety can be 1, 2, 3, 4, 5 or more moieties of a synthetic polymer. The synthetic polymer can be biodegradable or non-biodegradable. Biodegradable polymers useful as protracting moieties include, but are not limited to, poly(2-methacryloyloxyethyl phosphorylcholine) (PMPC) and poly[oligo(ethylene glycol) methyl ether methacrylate](POEGMA). Non-biodegradable polymers useful as protracting moieties include without limitation poly(ethylene glycol) (PEG), polyglycerol, poly(N-(2-hydroxypropyl)methacrylamide) (PHPMA), polyoxazolines and poly (N-vinylpyrrolidone) (PVP). A synthetic polymer can be polyethylene glycol (PEG). PEGylation can be done by chemical or enzymatic, site-specific coupling or by random coupling.

The individual mass (e.g., average molecular weight), or the total mass, of the one or more synthetic polymer moieties can be about 10-50, 10-20, 20-30, 30-40 or 40-50 kDa, or about 10, 20, 30, 40 or 50 kDa. The individual mass (e.g., average MW), or the total mass, of the one or more synthetic polymer moieties also can be greater than about 50 kDa, such as about 50-100, 50-60, 60-70, 70-80, 80-90 or 90-100 kDa, or about 60, 70, 80, 90 or 100 kDa. Moreover, the mass (e.g., average MW) of an individual synthetic polymer moiety can be less than about 10 kDa, such as about 1-5 or 5-10 kDa, or about 5 kDa. The individual mass (e.g., average MW), or the total mass, of the one or more synthetic polymer (e.g., PEG) moieties can be about 20 or 40 kDa.

Pharmaceutical Compositions

Additional embodiments of the disclosure relate to pharmaceutical compositions comprising an anti-CD79 antibody, or a pharmaceutically acceptable salt, solvate or hydrate thereof, and one or more pharmaceutically acceptable excipients or carriers. The compositions can optionally contain an additional therapeutic agent. In general, a pharmaceutical composition contains a therapeutically effective amount of an anti-CD79 antibody or a fragment thereof, one or more pharmaceutically acceptable excipients or carriers and optionally a therapeutically effective amount of an additional therapeutic agent, and is formulated for administration to a subject for therapeutic use.

Pharmaceutical compositions generally are prepared according to current good manufacturing practice (GMP), as recommended or required by, e.g., the Federal Food, Drug, and Cosmetic Act § 501(a)(2)(B) and the International Conference on Harmonisation Q7 Guideline.

Pharmaceutical compositions/formulations can be prepared in sterile form. For example, pharmaceutical compositions/formulations for parenteral administration by injection or infusion generally are sterile. Sterile pharmaceutical compositions/formulations are compounded or manufactured according to pharmaceutical-grade sterilization standards known to those of skill in the art, such as those disclosed in or required by the United States Pharmacopeia Chapters 797, 1072 and 1211, and 21 Code of Federal Regulations 211.

Pharmaceutically acceptable excipients and carriers include pharmaceutically acceptable substances, materials and vehicles. Non-limiting examples of types of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, stabilizers, antioxidants, preservatives, antimicrobial agents, antibacterial agents, antifungal agents, chelating agents, adjuvants, sweetening agents, flavoring agents, coloring agents, encapsulating materials and coating materials. The use of such excipients in pharmaceutical formulations is known in the art. For example, conventional vehicles and carriers include without limitation oils (e.g., vegetable oils such as olive oil and sesame oil), aqueous solvents {e.g., saline, buffered saline (e.g., phosphate-buffered saline [PBS]) and isotonic solutions (e.g., Ringer's solution)}, and organic solvents (e.g., dimethyl sulfoxide [DMSO] and alcohols [e.g., ethanol, glycerol and propylene glycol]). Except insofar as any conventional excipient or carrier is incompatible with an anti-CD79 antibody or a fragment thereof, the disclosure encompasses the use of conventional excipients and carriers in formulations containing an anti-CD79 antibody or a fragment thereof. See, e.g., Remington: The Science and Practice of Pharmacy, 21st Ed., Lippincott Williams & Wilkins (Philadelphia, Pa.) (2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Pre-formulation and Formulation, Gibson, Ed., CRC Press (Boca Raton, Fla.) (2004).

Appropriate formulation can depend on various factors, such as the route of administration chosen. Potential routes of administration of a pharmaceutical composition comprising an anti-CD79 antibody or a fragment thereof include without limitation oral, parenteral (including intradermal, subcutaneous, intramuscular, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal [e.g., by suppository], and vaginal [e.g., by suppository]). Topical formulations can be designed to produce a local or systemic therapeutic effect. In certain embodiments, an anti-CD79 antibody or a fragment thereof is administered parenterally (e.g., intravenously, subcutaneously, intramuscularly or intraperitoneally) by injection (e.g., as a bolus) or by infusion over a period of time.

Excipients and carriers that can be used to prepare parenteral formulations include without limitation solvents (e.g., aqueous solvents such as water, saline, physiological saline, buffered saline [e.g., phosphate-buffered saline], balanced salt solutions [e.g., Ringer's BSS] and aqueous dextrose solutions), isotonic/iso-osmotic agents (e.g., salts [e.g., NaCl, KCl and $CaCl_2$] and sugars [e.g., sucrose]), buffering agents and pH adjusters (e.g., sodium dihydrogen phosphate [monobasic sodium phosphate]/disodium hydrogen phosphate [dibasic sodium phosphate], citric acid/sodium citrate and L-histidine/L-histidine HCl), and emulsifiers (e.g., non-ionic surfactants such as polysorbates [e.g., polysorbate 20 and 80] and poloxamers [e.g., poloxamer 188]). Protein formulations and delivery systems are discussed in, e.g., A. J. Banga, Therapeutic Peptides and Proteins: Formulation, Processing, and Delivery Systems, 3rd Ed., CRC Press (Boca Raton, Fla.) (2015).

The excipients can optionally include one or more substances that increase protein stability, increase protein solubility, inhibit protein aggregation or reduce solution viscosity, or any combination or all thereof. Examples of such substances include without limitation hydrophilic amino acids (e.g., arginine and histidine), polyols (e.g., myo-inositol, mannitol and sorbitol), saccharides {e.g., glucose (including D-glucose [dextrose]), lactose, sucrose and trehalose}, osmolytes (e.g., trehalose, taurine, amino acids [e.g., glycine, sarcosine, alanine, proline, serine, β-alanine and γ-aminobutyric acid], and betaines [e.g., trimethylglycine and trimethylamine N-oxide]), and non-ionic surfactants {e.g., alkyl polyglycosides, ProTek® alkylsaccharides (e.g., a monosaccharide [e.g., glucose] or a disaccharide [e.g., maltose or sucrose] coupled to a long-chain fatty acid or a corresponding long-chain alcohol), and polypropylene glycol/polyethylene glycol block co-polymers (e.g., poloxamers [e.g., Pluronic™ F-68], and Genapol® PF-10 and variants thereof)}. Because such substances increase protein solubility, they can be used to increase protein concentration in a formulation. Higher protein concentration in a formulation is particularly advantageous for subcutaneous administration, which has a limited volume of bolus administration (e.g., ≤about 1.5 mL). In addition, such substances can be used to stabilize proteins during the preparation, storage and reconstitution of lyophilized proteins.

For parenteral (e.g., intravenous, subcutaneous or intramuscular) administration, a sterile solution or suspension of an anti-CD79 antibody in an aqueous solvent containing one or more excipients can be prepared beforehand and can be provided in, e.g., a pre-filled syringe. Alternatively, an anti-CD79 antibody can be dissolved or suspended in an aqueous solvent that can optionally contain one or more excipients prior to lyophilization (freeze-drying). Shortly prior to parenteral administration, the lyophilized anti-CD79 antibody stored in a suitable container (e.g., a vial) can be reconstituted with, e.g., sterile water that can optionally contain one or more excipients. If the anti-CD79 antibody is to be administered by infusion (e.g., intravenously), the solution or suspension of the reconstituted anti-CD79 antibody can be added to and diluted in an infusion bag containing, e.g., sterile saline (e.g., about 0.9% NaCl).

Excipients that enhance transmucosal penetration of smaller proteins include without limitation cyclodextrins, alky saccharides (e.g., alkyl glycosides and alkyl maltosides [e.g., tetradecylmaltoside]), and bile acids (e.g., cholic acid, glycocholic acid, taurocholic acid, deoxycholic acid, glycodeoxycholic acid, chenodeoxycholic acid and dehydrocholic acid).

Excipients that enhance transepithelial or transdermal penetration of smaller proteins include without limitation chemical penetration enhancers (CPEs, including fatty acids [e.g., oleic acid]), cell-penetrating peptides {CPPs, including arginine-rich CPPs [e.g., polyarginines such as $R_6$-$R_{11}$ (e.g., $R_6$ and $R_9$) and TAT-related CPPs such as TAT (49-57)] and amphipathic CPPs [e.g., Pep-1 and penetratin]}, and skin-penetrating peptides (SPPs, such as the skin-penetrating and cell-entering [SPACE] peptide). Transdermal penetration of smaller proteins can be further enhanced by use of a physical enhancement technique, such as iontophoresis, cavitational or non-cavitational ultrasound, electroporation, thermal ablation, radio frequency, microdermabrasion, microneedles or jet injection. US 2007/0269379 provides an extensive list of CPEs. F. Milletti, Drug Discov. Today, 17:850-860 (2012) is a review of CPPs. R. Ruan et al., Ther. Deliv., 7:89-100 (2016) discuss CPPs and SPPs for transdermal delivery of macromolecules, and M. Prausnitz and R. Langer, Nat. Biotechnol., 26:1261-1268 (2008) discuss a variety of transdermal drug-delivery methods.

An anti-CD79 antibody can be delivered from a sustained-release composition. As used herein, the term "sustained-release composition" encompasses sustained-release, prolonged-release, extended-release, slow-release and controlled-release compositions, systems and devices. Protein delivery systems are discussed in, e.g., Banga (supra). A sustained-release composition can deliver a therapeutically effective amount of an anti-CD79 antibody over a prolonged time period. In some embodiments, a sustained-release composition delivers an anti-CD79 antibody over a period of at least about 3 days, 1 week, 2 weeks, 3 weeks, 1 month (4 weeks), 6 weeks, 2 months, 3 months or longer. A sustained-release composition can be administered, e.g., parenterally (e.g., intravenously, subcutaneously or intramuscularly).

A sustained-release composition of a protein can be in the form of, e.g., a particulate system, a lipid or oily composition, or an implant. Particulate systems include without limitation nanoparticles, nanospheres, nanocapsules, microparticles, microspheres and microcapsules. Nanoparticulate systems generally have a diameter or an equivalent dimension smaller than about 1 μm. In certain embodiments, a nanoparticle, nanosphere or nanocapsule has a diameter or an equivalent dimension of no more than about 500, 400 or 300 nm, or no more than about 200, 150 or 100 nm. In some embodiments, a microparticle, microsphere or microcapsule has a diameter or an equivalent dimension of about 1-200, 100-200 or 50-150 μm, or about 1-100, 1-50 or 50-100 μm. A nano- or microcapsule typically contains the therapeutic agent in the central core, while the therapeutic agent typically is dispersed throughout a nano- or microparticle or sphere. In certain embodiments, a nanoparticulate system is administered intravenously, while a microparticulate system is administered subcutaneously or intramuscularly.

In some embodiments, a sustained-release particulate system or implant is made of a biodegradable polymer or/and a hydrogel. In certain embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. Non-limiting examples of polymers of which a hydrogel can be composed include polyvinyl alcohol, acrylate polymers (e.g., sodium polyacrylate), and other homopolymers and copolymers having a relatively large number of hydrophilic groups (e.g., hydroxyl or/and carboxylate groups). The biodegradable polymer of the particulate system or implant can be selected so that the polymer substantially completely degrades around the time the period of treatment is expected to end, and so that the byproducts of the polymer's degradation, like the polymer, are biocompatible.

Alternatively, a sustained-release composition of a protein can be composed of a non-biodegradable polymer. Examples of non-biodegradable polymers include without limitation poloxamers (e.g., poloxamer 407). Sustained-release compositions of a protein can be composed of other natural or synthetic substances or materials, such as hydroxyapatite.

Sustained-release lipid or oily compositions of a protein can be in the form of, e.g., liposomes, micelles (e.g., those composed of biodegradable natural or/and synthetic polymers, such as lactosomes), and emulsions in an oil.

A sustained-release composition can be formulated or designed as a depot, which can be injected or implanted, e.g., subcutaneously or intramuscularly. A depot can be in the form of, e.g., a polymeric particulate system, a polymeric implant, or a lipid or oily composition. A depot formulation can comprise a mixture of a protein and, e.g., a biodegradable polymer [e.g., poly(lactide-co-glycolide)] or a semi-biodegradable polymer (e.g., a block copolymer of lactic acid and PEG) in a biocompatible solvent system, whether or not such a mixture forms a particulate system or implant.

A pharmaceutical composition can be presented in unit dosage form as a single dose wherein all active and inactive ingredients are combined in a suitable system, and components do not need to be mixed to form the composition to be administered. The unit dosage form generally contains an effective dose of the therapeutic agent. A representative example of a unit dosage form is a single-use pen comprising a pre-filled syringe, a needle and a needle cover for parenteral (e.g., intravenous, subcutaneous or intramuscular) injection of the therapeutic agent.

Alternatively, a pharmaceutical composition can be presented as a kit in which the therapeutic agent, excipients and carriers (e.g., solvents) are provided in two or more separate containers (e.g., ampules, vials, tubes, bottles or syringes) and need to be combined to form the composition to be administered. The kit can contain instructions for storing, preparing and administering the composition (e.g., a solution to be injected intravenously or subcutaneously).

A kit can contain all active and inactive ingredients in unit dosage form or the active ingredient and inactive ingredients in two or more separate containers, and can contain instructions for administering or using the pharmaceutical composition to treat a medical condition.

In some embodiments, a kit contains an anti-CD79 antibody or a pharmaceutical composition comprising the same, and instructions for administering or using the anti-CD79 antibody or the pharmaceutical composition comprising the same to treat an antibody-associated condition.

Uses of Anti-CD79 Antibodies

The anti-CD79 antibodies described above can be administered to subjects suffering from antibody-associated conditions (e.g., diseases, disorders and/or syndromes). When the subject is a human, the anti-CD79 antibody can be a chimeric mouse-human antibody, or a humanized antibody. Such chimeric or humanized antibodies are described above. Antibody-associated conditions include, for example, autoimmune diseases, certain allergies (antibody associated allergies), certain kinds of type I diabetes, etc. Autoimmune diseases that can be treated with the anti-CD79 antibodies include, for example, systemic lupus erythematosus (SLE), inflammatory bowel disease (e.g., Crohn's disease and ulcerative colitis), rheumatoid arthritis, multiple sclerosis, Grave's disease, CREST syndrome, systemic sclerosis, celiac disease, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen scleroses, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, etc. Other antibody associated conditions that can be treated with the anti-CD79 antibodies include, for example, allergies (antibody associated allergies), amyloidosis, certain forms of transplant rejection, etc. These and other undesired antibody-associated conditions can be treated by administering one or more of the anti-CD79 antibodies described herein to a subject suffering from the undesired antibody-associated condition.

The anti-CD79 antibodies described herein can induce an anergic state in the B-cells of a subject, and thus can be used to treat certain autoimmune diseases. For example, autoimmune diseases associated with anti-self antibody reactions can be treated with the anti-CD79 antibodies as the anergic state induced will prevent the anti-self antibodies from being produced. The anti-CD79 antibodies described herein also can be used to induce an anergic state in any condition that has an undesired antibody response. The anti-CD79 antibodies described herein can be used to induce an anergic state in B-cells. The anti-CD79 antibodies described herein can be used to inhibit the proliferation of B-cells.

The anti-CD79 antibodies described herein can be used to identify and/or isolate B-cells in a sample and/or a subject. For example, the anti-CD79 antibodies described herein can be used to diagnose B-cell malignancies or other lymphoproliferative disorders, and/or can be used to as a vehicle to selectively transport agents to B-cell malignancies.

The anti-CD79 antibodies described herein can be used to treat B-cell malignancies directly, and/or can be used to construct cytotoxic T cells expressing chimeric T cell receptors (CAR-T) for treatment of CD79 positive B-cell malignancies. Chimeric antigen receptors (CAR) can be made using the antigen binding portions of the anti-CD79 antibodies described herein, as the antigen binding domain/portion of the CAR. These anti-CD79 CARs can be placed in immune cells, such as T-cells or natural killer cells, and the anti-CD79 immune cells can be used to treat diseases caused by cells that express CD79. Such diseases include, for example, CD79 positive hematopoietic cancers (e.g., lymphomas, leukemias, myelomas).

The therapeutically effective amount and the frequency of administration of, and the length of treatment with, an anti-CD79 antibody disclosed herein to treat an antibody-associated condition may depend on various factors, including the nature and severity of the condition, the potency of the antibody, the mode of administration, the age, body weight, general health, gender and diet of the subject, and the response of the subject to the treatment, and can be determined by the treating physician. The therapeutically effective amount of the antibody (e.g., anti-CD79 antibody LB517/LB519) for the treatment of an antibody-associated condition can be from about 1, 5 or 10 mg to about 200 mg, from about 1, 5 or 10 mg to about 150 mg, from about 1, 5 or 10 mg to about 100 mg, or from about 1, 5 or 10 mg to about 50 mg, or as deemed appropriate by the treating physician, which can be administered in a single dose or in divided doses. The therapeutically effective amount of the antibody can be about 1-5 mg, 5-10 mg, 10-20 mg, 20-30 mg, 30-40 mg, 40-50 mg, 50-100 mg, 100-150 mg or 150-200 mg. The therapeutically effective amount of the antibody can be about 1, 5, 10, 15, 20, 25, 30, 40, 50, 60, 70, 80, 90, 100, 150 or 200 mg. The therapeutically effective amount of the antibody can be about 1-5 mg, 5-10 mg or 10-50 mg. The therapeutically effective amount of the antibody (e.g., anti-CD79 antibody LB517/LB519) for the treatment of an antibody-associated condition can be about 0.01-0.1 mg/kg, 0.1-0.5 mg/kg, 0.5-1 mg/kg, 1-2 mg/kg or 2-3 mg/kg body weight, or as deemed appropriate by the treating physician. The therapeutically effective amount of the antibody can be about 0.01-0.1 mg/kg, 0.1-0.5 mg/kg or 0.5-1 mg/kg body weight.

An anti-CD79 antibody can be administered in any suitable frequency to treat an antibody-associated condition. The antibody (e.g., anti-CD79 antibody LB517/LB519) can be administered once daily, once every 2 days, once every 3 days, twice weekly, once weekly, once every 2 weeks, once every 3 weeks, once monthly, once every 6 weeks, once every 2 months or once every 3 months, or as deemed appropriate by the treating physician. The antibody or can be administered once weekly or once every 2 weeks.

Likewise, an anti-CD79 antibody can be administered for any suitable length of time, or in any suitable total number of doses, to treat an antibody-associated condition. The antibody (e.g., anti-CD79 antibody LB517/LB519) is administered over a period of at least about 1 week, 2 weeks, 1 month (4 weeks), 6 weeks, 2 months, 3 months, 6 months, 1 year, 2 years, 3 years or longer, or as deemed appropriate by the treating physician. The antibody-associated condition can be a chronic condition. A chronic condition can exist for, e.g., at least about 6 weeks or 2 months or longer. The antibody can be administered over a period of at least about 6 weeks, 2 months, 3 months or 6 months. 1, 2, 3, 4, 5 or 6 doses of the antibody (e.g., anti-CD79 antibody LB517/LB519) can be administered for the entire treatment regimen. 1, 2 or 3 doses of the antibody can be administered for the entire treatment regimen.

An anti-CD79 antibody (e.g., anti-CD79 antibody LB517/LB519) can also be administered in an irregular manner to treat an antibody-associated condition. For example, the antibody or fragment thereof can be administered 1, 2, 3, 4, 5 or more times in a period of 1 week, 2 weeks, 3 weeks, 1 month, 2 months or 3 months in an irregular manner. Furthermore, an anti-CD79 antibody (e.g., anti-CD79 antibody LB517/LB519) can be taken pro re nata (as needed) for treatment of an antibody-associated condition. For instance, the antibody can be administered 1, 2, 3, 4, 5 or more times, whether in a regular or irregular manner, for treatment of hypertension until blood pressure is lowered to a certain level. Once blood pressure is reduced to a certain level, dosing of the antibody can optionally be discontinued. If blood pressure reaches or surpasses a certain level, administration of the antibody, whether in a regular or irregular manner, can be resumed. The appropriate dosage of, frequency of dosing of and length of treatment with the antibody can be determined by the treating physician.

For a more rapid establishment of a therapeutic level of an anti-CD79 antibody at least one loading dose of the antibody or fragment thereof can be administered prior to the maintenance dose. A loading dose of the antibody (e.g., anti-CD79 antibody LB517/LB519) can be administered, followed by (i) one or more additional loading doses and then one or more therapeutically effective maintenance doses, or (ii) one or more therapeutically effective maintenance doses without an additional loading dose, as deemed appropriate by the treating physician. A loading dose of a drug can be larger (e.g., about 1.5, 2, 3, 4 or 5 times larger) than a subsequent maintenance dose and is designed to establish a therapeutic level of the drug more quickly. The one or more therapeutically effective maintenance doses can be any therapeutically effective amount described herein. The loading dose can be about 2 or 3 times larger than the maintenance dose. A loading dose of the antibody can be administered on day 1, and a maintenance dose of the antibody can be administered, e.g., once weekly or once every 2 weeks thereafter for the duration of treatment. The antibody (e.g., anti-CD79 antibody LB517/LB519) can be administered in a loading dose of about 2-10 mg, 10-20 mg or 20-100 mg, or about 3-15 mg, 15-30 mg or 30-150 mg, on day 1, followed by a maintenance dose of about 1-5 mg, 5-10 mg or 10-50 mg once weekly or once every 2 weeks for the duration of treatment (e.g., for at least about 2, 3 or 6 months), where the loading dose is about 2 or 3 times larger than the maintenance dose and the antibody or fragment thereof is administered parenterally (e.g., intravenously, subcutaneously or intramuscularly).

Two (or more) loading doses of the antibody can be administered prior to the maintenance dose. A first loading dose of the antibody or fragment thereof can be administered on day 1, a second loading dose can be administered, e.g., about 1 or 2 weeks later, and a maintenance dose can be administered, e.g., once weekly or once every 2 weeks thereafter for the duration of treatment. The first loading dose can be about 3 or 4 times larger than the maintenance dose, and the second loading dose can be about 2 times larger than the maintenance dose. The antibody (e.g., anti-CD79 antibody LB517/LB519) can be administered in a first loading dose of about 3-15 mg, 15-30 mg or 30-150 mg, or about 4-20 mg, 20-40 mg or 40-200 mg, on day 1, in a second loading dose of about 2-10 mg, 10-20 mg or 20-100 mg about 1 or 2 weeks later, followed by a maintenance dose of about 1-5 mg, 5-10 mg or 10-50 mg once weekly or once every 2 weeks for the duration of treatment (e.g., for at least about 2, 3 or 6 months), where the first loading dose can be about 3 or 4 times larger than the maintenance dose, the second loading dose can be about 2 times larger than the maintenance dose, and the antibody or fragment thereof can be administered parenterally (e.g., intravenously, subcutaneously or intramuscularly).

Combination Therapies with Additional Therapeutic Agents

The disclosure provides a method of treating an antibody-associated condition, comprising administering to a subject in need of treatment a therapeutically effective amount of an anti-CD79 antibody described herein, optionally in combination with an additional therapeutic agent. The disclosure further provides an anti-CD79 antibody described herein, or a composition comprising an anti-CD79 antibody described herein, for use as a medicament, optionally in combination with an additional therapeutic agent. In addition, the disclosure provides for the use of an anti-CD79 antibody described herein in the preparation of a medicament, optionally in combination with an additional therapeutic agent. In some embodiments, the medicament is used for treatment of an antibody-associated condition.

One or more additional therapeutic agents can optionally be used in combination with an anti-CD79 antibody (e.g., anti-CD79 antibody LB517/LB519) to treat an antibody-associated condition. The optional additional therapeutic agent(s) can be administered to a subject concurrently with (e.g., in the same composition as the antibody or fragment thereof or in separate compositions) or sequentially to (before or after) administration of the antibody.

The optional additional therapeutic agent(s) can be selected from immunosuppressive agents, anti-inflammatory agents, allergy drugs, and combinations thereof. One or more immunosuppressive agents can be used in combination with an anti-CD769 antibody (e.g., anti-CD79 antibody LB517/LB519) to treat an antibody associate condition. Such immunosuppressive agents can include, for example, anti-CD20 antibodies (e.g., rituximab), calcineurin inhibitors (e.g., tacrolimus, cyclosporine, etc.), antiproliferative agents or IDMH inhibitors (e.g., mycophenolate mofetil, mycophenolate sodium, azathioprine, leflunomide, etc.), mTOR inhibitors (e.g., Sirolimus, everolimus, etc.), steroids (e.g., corticosteroids such as prednisone, budesonide, prednisolone, etc.), and biologics (e.g., abatacept, adalimumab, anakinra, certolizumab, etanercept, infliximab, ixekizumab, natalizumab, rituximab, secukinumab, tocilizumab, uestekinumab, vedolizumab, basiliximab, daclizumab, muromonab). Biologics can also include, for example, CTLA 4 fusion proteins, anti-TNFα antibodies, IL-1 receptor antagonist protein, TNF receptor fusion proteins, anti-IL17A antibodies, anti-α4 integrin antibodies, anti-IL6 receptor antibodies, anti-p40 subunit of IL12/IL23 antibodies, anti-$α_4β_7$ integrin antibodies, anti-CD25 antibodies, and anti-CD3 antibodies.

One or more anti-inflammatory agents can used in combination with an anti-CD79 antibody (e.g., anti-CD79 antibody LB517/LB519) to treat an antibody-associated condition that has a component of inflammation. The one or more anti-inflammatory agents can include, for example, an inhibitor of a pro-inflammatory cytokine or a receptor therefor or the production thereof (e.g., TNF-α or/and IL-6 or IL-6R). Other anti-inflammatory agents include, for example: non-steroidal anti-inflammatory drugs (NSAIDs), immunomodulators, immunosuppressants, anti-inflammatory cytokines and compounds that increase their production, inhibitors of pro-inflammatory cytokines or receptors therefor, inhibitors of the production of pro-inflammatory cytokines or receptors therefor, inhibitors of pro-inflammatory transcription factors or their activation or expression, inhibitors of pro-inflammatory prostaglandins (e.g., prostaglandin $E_2$ [$PGE_2$]) or receptors therefor (e.g., $EP_3$) or the production thereof, inhibitors of leukotrienes or receptors therefor or the production thereof, inhibitors of phospholipase A2 (e.g., secreted and cytosolic PLA2), suppressors of C-reactive protein (CRP) activity or level, mast cell stabilizers, phosphodiesterase inhibitors, specialized pro-resolving mediators (SPMs), other kinds of anti-inflammatory agents, and analogs, derivatives, fragments and salts thereof.

Non-steroidal anti-inflammatory drugs (NSAIDs) include without limitation: acetic acid derivatives, anthranilic acid derivatives (fenamates), enolic acid derivatives (oxicams), propionic acid derivatives, salicylates, COX-2-selective inhibitors, other kinds of NSAIDs, such as monoterpenoids (e.g., eucalyptol and phenols [e.g., carvacrol]), anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) (e.g., chebulagic acid, licofelone, 2-(3,4,5-trimethoxyphenyl)-4-(N-methylindol-3-yl)thiophene, and di-tert-butylphenol-based compounds [e.g., DTPBHZ, DTPINH, DTPNHZ and DTPSAL]); and analogs, derivatives and salts thereof.

The glucocorticoid class of corticosteroids has anti-inflammatory and immunosuppressive properties. Glucocorticoids include without limitation hydrocortisone types, halogenated steroids, carbonates, and analogs, derivatives and salts thereof.

The optional additional therapeutic agent(s) independently can be administered in any suitable mode. Potential modes of administration include without limitation oral, parenteral (including intradermal, subcutaneous, intramuscular, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal [e.g., by suppository] and vaginal [e.g., by suppository]). In some embodiments, the optional additional therapeutic agent(s)

independently are administered orally or parenterally (e.g., intravenously, subcutaneously or intramuscularly).

One or more anti-allergy agents can be used in combination with an anti-CD79 antibody (e.g., anti-CD79 antibody LB517/LB519) to treat an antibody-associated condition. Such anti-allergy agents can include, for example, antihistamines (e.g., cetirizine, fexofenadine, levocetirizine, loratidine, bormpheniramine, chlorpheniramine, celmastine, diphenhydramine, ketotifen, naphazoline, pheniramine, desloratadine, azelastine, epinastine, olopatadine), decongestants (e.g., pseudoephedrine, phenylephrine, oxymetazoline), steroids (e.g., beclomethasone, ciclesonide, fluticasone furoate, mometasone, budesonide, triamcinolone, dexamethasone, loteprednol, prednisone epocrates), mast cell stabilizers (e.g., cromolyn sodium, lodoxamide-tromethamine, nedocromil, pemirolast), and leukotriene modifiers (e.g., monteleukast).

One or more anti-rejection drugs for a transplant can be used in combination with an anti-CD79 antibody (e.g., anti-CD79 antibody LB517/LB519) to treat a subject following a transplant procedure. Such anti-rejection drugs can include, for example, calcineurin inhibitors, antiproliferative agents or IDMH inhibitors, mTOR inhibitors, and steroids.

The optional additional therapeutic agent(s) independently can be administered in any suitable frequency, including without limitation daily (1, 2 or more times per day), every two or three days, twice weekly, once weekly, every two weeks, every three weeks, monthly, every two months or every three months, or in an irregular manner or on an as-needed basis. The dosing frequency can depend on, e.g., the mode of administration chosen. The length of treatment with the optional additional therapeutic agent(s) can be determined by the treating physician and can independently be, e.g., at least about 1 day, 2 days, 3 days, 4 days, 1 week, 2 weeks, 3 weeks, 4 weeks (1 month), 6 weeks, 2 months, 3 months, 6 months, 1 year, 2 years, 3 years or longer.

Diagnostic Uses of Anti-CD79 Antibodies

The anti-CD79 antibodies disclosed herein are also useful in diagnostic and prognostic assessment of B-cell associated disorders. Furthermore, such antibodies can be used to facilitate treatment decisions.

An anti-CD79 antibody can be employed to detect the presence of B-cell lineage cells in an original or processed sample obtained from a subject. A biological sample can comprise, e.g., blood, plasma, serum, urine, cerebrospinal fluid (CSF), cells or tissue. A sample can be analyzed directly, extracted before analysis, or expanded in volume by the addition of a suitable solvent.

A biological sample can be contacted with an anti-CD79 antibody, and the sample is screened to detect binding of the antibody or fragment thereof to B-cells. Detection of such binding indicates the presence of B-cells in the sample. The anti-CD79 antibody can be labeled with a detectable agent (e.g., a fluorescent dye), so that binding of the antibody to B-cells evokes a signal. B-cells in a biological sample can be immobilized on a surface prior to introduction of a labeled anti-CD79 antibody (a direct assay), and the amount of the signal, corresponding to the amount of labeled antibody or fragment thereof bound to B-cells, correlates to the amount of B-cells in the sample. B-cells in a biological sample can be captured by an unlabeled first antibody immobilized on a surface, and then detected by a labeled second antibody that binds to the captured B-cells and produces a signal in proportion to the amount of captured B-cell (a sandwich assay), where the unlabeled first antibody and the labeled second antibody bind to different epitopes on the B-cell, and the unlabeled first antibody or/and the labeled second antibody independently can be an anti-CD79 antibody disclosed herein.

B-cells in a biological sample can be detected in a competitive assay. A sample (optionally suspended in a buffer) can be mixed with a labeled anti-CD79. The resulting mixture can then be contacted with a B-cell marker-coated substrate. The greater the number of B-cells in the sample, the more antibody/B-cell complexes are formed and the less unbound (free) antibody is available to bind to B-cell marker on the substrate ("competition"), and hence the lower the signal produced.

In the direct, sandwich and competitive assays described above, the primary anti-CD79 antibody can be labeled with a detectable agent. Alternatively, in the direct, sandwich and competitive assays, the primary anti-CD79 antibody can be unlabeled and can be bound by a labeled secondary antibody (e.g., one that binds to the Fc region of the primary antibody) after binding of the primary antibody to B-cell. If the secondary antibody is conjugated to an enzyme, addition of a substrate of the enzyme results in an enzyme/substrate reaction that generates a signal (e.g., a chromogenic, fluorescent or electrochemical signal). The absorbance, fluorescence or electrochemical signal (e.g., current) of the solid support (e.g., a plate well or a bead) is measured to determine the presence and number of B-cells in the sample. Non-limiting examples of substrates of horseradish peroxidase (HRP) include 3-amino-9-ethylcarbazole (AEC), 3,3'-diaminobenzidine (DAB) and 3,3',5,5'-tetramethylbenzidine (TMB), those of alkaline phosphatase include 5-bromo-4-chloro-3-indolyl phosphate (BCIP), and those of β-glucuronidase include 5-bromo-4-chloro-3-indolyl-β-D-glucuronide (X-Gluc). Such an assay is called an enzyme-linked immunosorbent assay (ELISA).

Detectable agents include without limitation chromophores {e.g., dyes, stains, pigments and chromogens (e.g., 3-amino-9-ethylcarbazole [AEC], 5-bromo-4-chloro-3-indolyl phosphate [BCIP], 3,3'-diaminobenzidine [DAB] and 3,3',5,5'-tetramethylbenzidine [TMB])}, fluorophores/fluorochromes (e.g., fluorescent dyes such as fluorescein, fluorescein isothiocyanate and rhodamine), chemiluminescent compounds (e.g., luciferin and luminol), radioisotopes (e.g., $^{3}$H, $^{14}$C, $^{32}$P, $^{35}$S and $^{125}$I), radioactive elements (e.g., technetium), electron-dense compounds, magnetic substances and particles (e.g., paramagnetic and superparamagnetic ones), magnetic resonance imaging (MRI) contrast agents (e.g., gadolinium-containing ones), enzymes (e.g., horseradish peroxidase [HRP], alkaline phosphatase, luciferase, β-glucuronidase and β-galactosidase), haptens and toxins.

The anti-CD79 antibodies described herein can be employed in a variety of immunometric assays. Such assays include without limitation chromogenic, fluorescence, chemiluminescence, light scattering, radiolabeled, electrochemical, enzyme, precipitation, agglutination, coagulation, Western blot, grid blot, tissue blot, dot blot, dip stick, and biosensor assays. See, e.g., Principles and Practice of Immunoassays, C. Price and D. Newman (Eds.), Stockton Press (1997); and The Immunoassay Handbook, $2^{nd}$ Ed., D. Wild (Ed.), Nature Publishing Group (2001). Furthermore, the anti-CD79 antibodies can be utilized in imaging, such as by MRI.

Detection and measurement of the amount of B-cells in a biological sample can facilitate diagnosis, prognosis and treatment of B-cell-associated disorders. In some embodiments, a disorder is associated with an elevated level of B-cells, and an elevated level of B-cells in a sample from a subject compared to the level of B-cells in a corresponding sample from other subject(s) without the disorder is indicative of diagnosis of the disorder in the subject. The reference B-cell level for purposes of diagnosis of the disorder can be determined based on, e.g., a comparison of the B-cell level in a corresponding sample from a statistically or epidemiologically significant number of subjects without the disorder to the B-cell level in a corresponding sample from a statistically or epidemiologically significant number of subjects with the disorder. Similarly, for treatment and prognostic purposes the level of B-cells in a sample from a subject can be compared to, e.g., a scale of B-cell levels correlated with the severity of a B-cell-associated disorder to determine the current severity of the disorder and to predict the probable course or outcome (e.g., progression or regression) of the disorder.

In addition, detection and measurement of the amount of B-cells in a biological sample can facilitate treatment decisions. In some embodiments, the amount of an anti-CD79 antibody administered to a subject or/and the frequency of administration of the antibody to the subject are maintained or adjusted (increased or reduced), or administration of the antibody or fragment thereof to the subject is stopped, based on the presence, absence, amount or level of B-cells in a sample from the subject.

In some embodiments, a kit contains an anti-CD79 antibody that can optionally be labeled with a detectable agent, and optionally instructions for using the anti-CD79 antibody for a diagnostic application (e.g., in an immunoassay).

Production of Anti-CD79 Antibodies

The disclosure provides polynucleotides comprising nucleic acid sequences that encode anti-CD79 antibodies described herein. A polynucleotide can comprise a nucleic acid sequence that encodes the $V_H$ domain or/and the $V_L$ domain of an anti-CD79 mAb. A polynucleotide can comprise a nucleic acid sequence that encodes the heavy chain or/and the light chain of an anti-CD79 mAb.

The disclosure further provides constructs (which may also be called expression or cloning constructs) comprising nucleic acid sequences that encode anti-Cd79 antibodies described herein. Suitable constructs include, but are not limited to, plasmids, cosmids, bacterial artificial chromosomes, yeast artificial chromosomes, lambda phages (e.g., those with lysogeny genes deleted), and viruses. A construct can be present in a cell episomally or integrated into a chromosome (either way the construct remains and is still a construct, a plasmid and a vector).

Various construct systems can be employed. One class of constructs utilize DNA elements derived from animal viruses such as adenovirus, baculovirus, bovine papilloma virus, polyoma virus, SV40 virus, vaccinia virus, and retroviruses (e.g., MMTV, MOMLV and rous sarcoma virus). Another class of constructs utilize RNA elements derived from RNA viruses such as eastern equine encephalitis virus, flaviviruses and Semliki Forest virus.

A construct can comprise various other elements for optimal expression of mRNA in addition to a nucleic acid sequence that encodes, e.g., the $V_H$ domain or/and the $V_L$ domain, or the heavy chain or/and the light chain, of an anti-Cd79 mAb. For example, a construct can contain a transcriptional promoter, a promoter plus an operator, an enhancer, an open reading frame with or without intron(s) or/and exon(s), a termination signal, a splice signal, a secretion signal sequence or a selectable marker (e.g, a gene conferring resistance to an antibiotic or cytotoxic agent), or any combination or all thereof.

The disclosure also provides host cells comprising or expressing constructs that encode anti-CD79 antibodies described herein. Suitable host cells include, but are not limited to, eukaryotic cells, mammalian cells (e.g., BHK, CHO, COS, HEK293, HeLa, MDCKII and Vero cells), insect cells (e.g., Sf9 cells), yeast cells and bacterial cells (e.g., *E. coli* cells). The host cell can be a mammalian cell (e.g., a CHO cell or a HEK293 cell).

A host cell can comprise or express a construct that encodes the $V_H$ domain or the $V_L$ domain, or the heavy chain or the light chain, of an anti-CD79 mAb. A host cell can comprise or express a single construct that encodes the $V_H$ domain and the $V_L$ domain, or the heavy chain and the light chain, of an anti-CD79 mAb. The same host cell or separate host cells can comprise or express a construct that encodes the $V_H$ domain or the heavy chain of an anti-CD79 mAb, and a separate construct that encodes the $V_L$ domain or the light chain of the mAb.

A construct can be transfected or introduced into a host cell by any method known in the art. Transfection agents and methods include without limitation calcium phosphate, cationic polymers (e.g., DEAE-dextran and polyethylenimine), dendrimers, fugene, cationic liposomes, electroporation, sonoporation, cell squeezing, gene gun, viral transfection and retroviral transduction.

Methods and conditions for culturing transfected host cells and recovering the recombinantly produced anti-CD79 antibody are known in the art, and may be varied or optimized depending on, e.g., the particular expression vector or/and host cell employed. The $V_H$ domain or/and the $V_L$ domain, or the heavy chain or/and the light chain, of an anti-CD79 mAb can be recombinantly produced. The heavy chain and the light chain of an anti-CD79 whole IgG1, IgG2 or IgG4, or the heavy chain and the light chain of an anti-CD79 Fab fragment optionally fused with a protracting moiety, are recombinantly produced.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The following examples are intended only to illustrate the disclosure. Other assays, studies, processes, protocols, procedures, methodologies, reagents and conditions may alternatively be used as appropriate.

EXAMPLES

Example 1. Creation of Chimeric Anti-CD79 Antibodies

A chimeric antibody HcLc was created from a mouse antibody that binds to CD79 with high specificity and high affinity. The $V_H$ domain and the $V_L$ domain of a mouse antibody (SEQ ID NOs: 1 and 2) were fused to human IgG2 $C_H1$, $C_H2$ and $C_H3$ domains or a human kappa $C_L$ domain, respectively.

Example 2. Creation of Humanized Anti-CD79 Antibodies

The mouse antibody that binds CD79 was also humanized. The CDRs of the heavy chain (IgG1) and the light chain (kappa) SEQ ID NOs: 3-8 were grafted to acceptor human framework sequences. Three of these CDRs (CDR- L1, CDR-L2, and CDR-H2) contain amino acid motifs (DG, DS, and NG) that can be undesirable. A different CDR-L1 is used with KSSQSLLDSSGKTYLN (SEQ ID NO: 57), and two different CDR-H2s are used with RIYPENGDTNY-AGKFKG (SEQ ID NO: 58), or RIYPESGDTNYAGKFKG (SEQ ID NO: 59). In addition, certain framework amino acid residues of mouse antibody were retained, including amino acids that are immediately adjacent to a CDR sequence-wise or are predicted to be within about 3 Å of a CDR in a 3D immunoglobulin model and may contact the antigen and support binding of the CDR to the antigen. Roughly about three mouse framework amino acid residues adjacent to a CDR were retained.

Human framework sequences were selected by aligning the mouse framework sequences with a database of human framework sequences to find the closest human homologs for each chain (generally about 65-70% sequence identity). The human VH1-2 framework was used as the human acceptor framework as most homologous to the mouse framework sequence for the heavy chain, and the VK2-30 was used as the human acceptor framework as most homologous to the mouse framework sequence for the light chain. Three different VL-FR2s were used WFQQRPGQSPRRLIY (SEQ ID NO: 60), WLQQRPGQSPRRLIY (SEQ ID NO: 61), OR WLQQRPGQSPKRLIY (SEQ ID NO: 62). Two amino acid changes were made in VH-FR1 QVQLVQS-GAEVKKPGASVKVSCKASGYAFS (SEQ ID NO: 63). Three different combinations of VH-FR2 and VH-FR3 were used VH-FR2 WVRQAPGQGLEWMG (SEQ ID NO: 64) and VH-FR3 RVTMTRDTSISTAYMELSRLRSDD-TAVYYCAR (SEQ ID NO: 65), VH-FR2 WVRQAPGQ-GLEWMG (SEQ ID NO: 64) and VH-FR3 RVTMTADT-SISTAYMELSRLRSDDTAVYYCAR (SEQ ID NO: 66), and VH-FR2 WVRQAPGQGLEWIG (SEQ ID NO: 67) and VH-FR3 RVTLTADKSISTAYMELSRLRSDDTAVYY-CAR (SEQ ID NO: 68).

Humanized heavy chains H1-H3 (SEQ ID NOs: 9-11) and L1-L3 (SEQ ID NOs: 18-20) were made and combinatorially mixed and matched to make a library of humanized clones (H1-H3 combinatorially mixed with L1-L3). Individual members were isolated and tested for affinity binding to CD79. The binding data obtained is listed in Table 1 below:

TABLE 1

Binding Affinity for Humanized Antibodies

| Loading Sample ID | KD (M) | kon(1/Ms) | kdis(1/s) | Full X^2 | Full R^2 |
|---|---|---|---|---|---|
| H1L2 | 4.5E−08 | 9.1E+04 | 4.1E−03 | 0.0208 | 0.9973 |
| H2L2 | 4.6E−08 | 1.0E+05 | 4.6E−03 | 0.0315 | 0.9943 |
| H1L3 | 4.9E−08 | 8.2E+04 | 4.0E−03 | 0.0264 | 0.9966 |
| H1L1 | 5.9E−08 | 9.2E+04 | 5.4E−03 | 0.0408 | 0.9922 |
| HcLc | 6.0E−08 | 9.3E+04 | 5.6E−03 | 0.0833 | 0.9857 |
| H2L3 | 6.1E−08 | 8.4E+04 | 5.1E−03 | 0.0679 | 0.9869 |
| H2L1 | 9.0E−08 | 7.9E+04 | 7.1E−03 | 0.0444 | 0.9895 |
| H3L3 | 1.3E−07 | 7.9E+04 | 1.1E−02 | 0.1020 | 0.9611 |
| H3L2 | 1.4E−07 | 6.1E+04 | 8.6E−03 | 0.1402 | 0.9726 |
| H3L1 | 2.9E−07 | 4.3E+04 | 1.3E−02 | 0.1566 | 0.9472 |

The lead antibody H1L2 (LB495/PRI47, SEQ ID NOs: 9 and 19) was selected.

Example 3. Affinity Maturation of Humanized Antibody H1L2 (LB495/PRI47, SEQ ID NOs: 9 and 19)

The humanized antibody H1L2 (SEQ ID NOs: 9 and 19) was affinity matured. Four phage display libraries were made, two from the heavy chain H1 (SEQ ID NO: 10) and two from the light chain L2 (SEQ ID NO: 20). Saturation mutagenesis was performed on the CDR3 to make CDR3 heavy and CDR3 light chain libraries, and error prone PCR was also used to randomly mutagenize each the H1 heavy and the L2 light chain to make a heavy chain library and a light chain library. Each heavy chain library was combined with the parent light chain L2 (SEQ ID NO: 19), and each light chain library was paired with the parent heavy chain H1 (SEQ ID NO: 9) to make phage display libraries of candidates for affinity maturation. Each library was panned against CD79 in a competition assay with the parent H1L2 antibody, and binding clones obtained in the panning were tested for affinity in an ELISA. A VH clone with a mutation in CDR3 (SEQ ID NO: 25) was selected, and VL clone with mutations at the same position of CDR3 (SEQ ID NOs: 28-31) were selected. These heavy and light chains were reformatted to full length IgG, produced from 293 cells, purified and then tested for binding.

The binding data for these full length IgGs is presented in Table 2 below:

TABLE 2

Binding Affinity for Affinity Matured Antibodies

| Loading Sample ID | KD (M) | Kon (1/Ms) | Kdis (1/s) | Full X^2 | Full R^2 |
|---|---|---|---|---|---|
| PRI43/PRI47 | 5.10E−09 | 8.41E+04 | 4.29E−04 | 0.1219 | 0.9989 |
| LB517/PRI47 | 3.55E−09 | 8.75E+04 | 3.11E−04 | 0.1046 | 0.9991 |
| LB495/518 | 3.64E−09 | 9.12E+04 | 3.32E−04 | 0.0725 | 0.9994 |
| LB495/519 | 3.14E−09 | 8.03E+04 | 2.52E−04 | 0.1107 | 0.9989 |
| LB495/520 | 3.76E−09 | 9.96E+04 | 3.74E−04 | 0.0723 | 0.9993 |
| LB495/521 | 3.65E−09 | 9.91E+04 | 3.62E−04 | 0.0502 | 0.9993 |
| LB517/518 | 2.24E−09 | 8.85E+04 | 1.99E−04 | 0.0533 | 0.9994 |
| LB517/519 | 2.00E−09 | 7.97E+04 | 1.59E−04 | 0.0834 | 0.9994 |
| LB517/520 | 2.40E−09 | 9.78E+04 | 2.34E−04 | 0.0720 | 0.9993 |
| LB517/521 | 2.30E−09 | 8.75E+04 | 2.01E−04 | 0.0736 | 0.9992 |

PRI 47 is light chain L2 (SEQ ID NO: 19), PRI 43 and LB495 are heavy chain H1 (SEQ ID NO: 9), LB517 is heavy chain LB509-C2 (SEQ ID NO: 25), LB518 is light chain LB511-A9 (SEQ ID NO: 28), LB519 is light chain LB511-F6 (SEQ ID NO: 30), LB520 is light chain LB511-F11 (SEQ ID NO: 31), and LB521 is light chain LB511-B6 (SEQ ID NO: 29).

The affinity matured antibodies exhibited higher affinities than the parent humanized antibody.

Example 4. Development of Antibody Cell Lines

CHO cells (Invitrogen) were cultured in serum-free medium (CD FortiCHO, Invitrogen) and were co-transfected with separate plasmids encoding the heavy chain and the light chain of an anti-CD79 antibody using Freestyle Max transfection reagent (Invitrogen). The antibody expression plasmids were linearized with restriction digestion by Sca I before transfection. Antibody expression in the conditioned medium was measured by ELISA.

The transfected cells were subjected to stable selection with 10 µg/ml of puromycin and 500 µg/ml of G418 for 2 weeks. After single cell cloning, the high production CHO cell clones were screened and isolated. Antibody production was assessed in shake flask cultures to be >500 mg/L.

Example 5. Recombinant Production of Humanized Anti-CD79 Antibodies

HEK293F cells (Invitrogen) were cultured in serum-free medium and were co-transfected with a plasmid encoding LB517 and a plasmid encoding LB519, or the plasmids expressing the other antibody variants. On day 5 post-transfection, cell culture supernatants were harvested and subjected to Protein A chromatography for antibody purification.

Example 6. Human CD79a/79b Knock-in Mice

C57BL/6 embryonic stem cells were engineered to replace the mouse CD79a and CD79b loci with nucleic acids encoding human CD79a and human CD79b. The engineered C57BL/6 ES cells were implanted into female C57BL/6 mice and C57BL/6 offspring were obtained that were human CD79a/b positive. Expression of human CD79a and CD79b on B-cells was confirmed using FACS with anti-human CD79 antibodies.

Figure 3A:
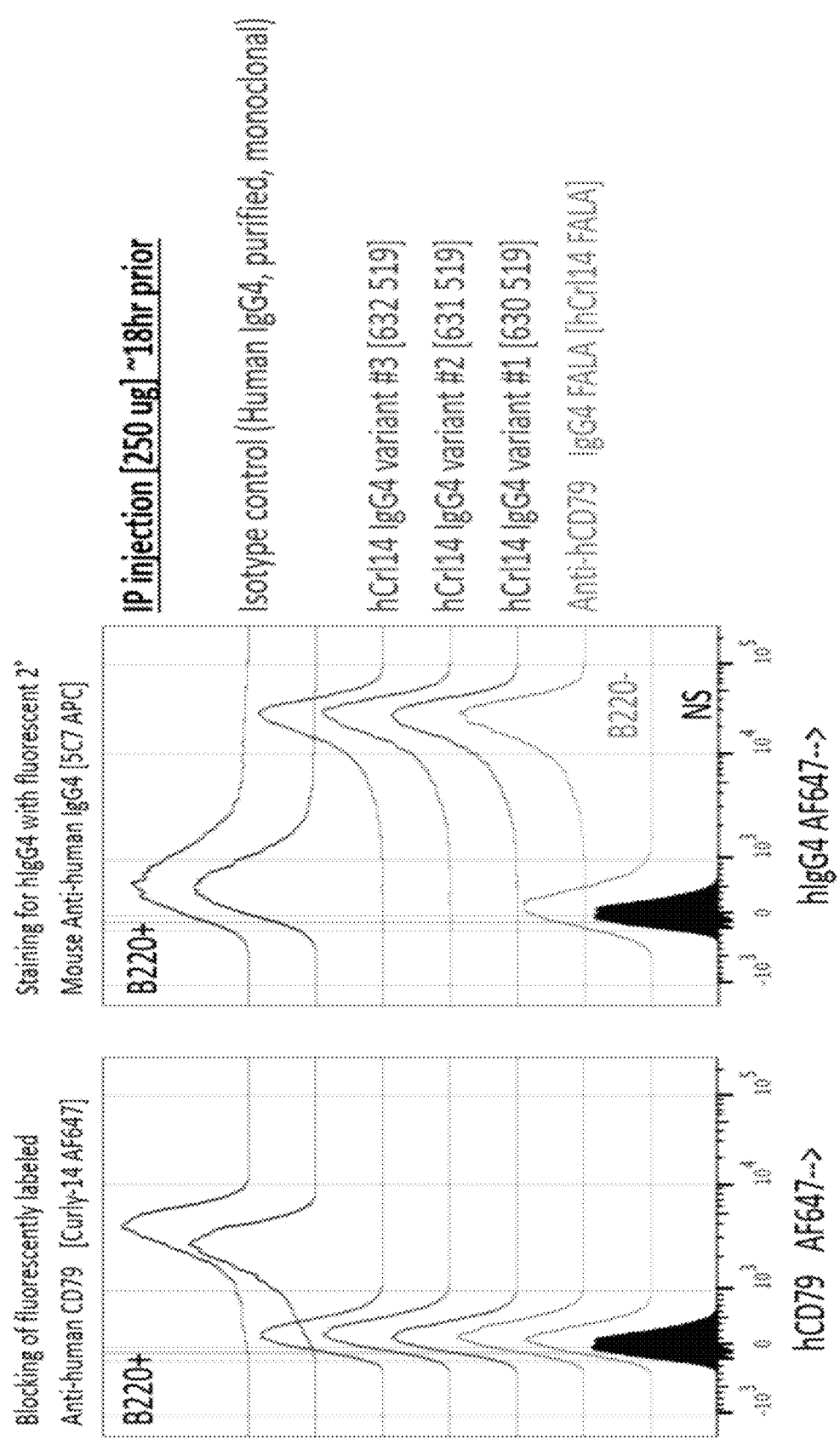
FIG. 3a shows competition binding between the antibody LB517/LB519 (hCurl4 FALA) and Curly-14 for binding to B cells.
Figure 3B:
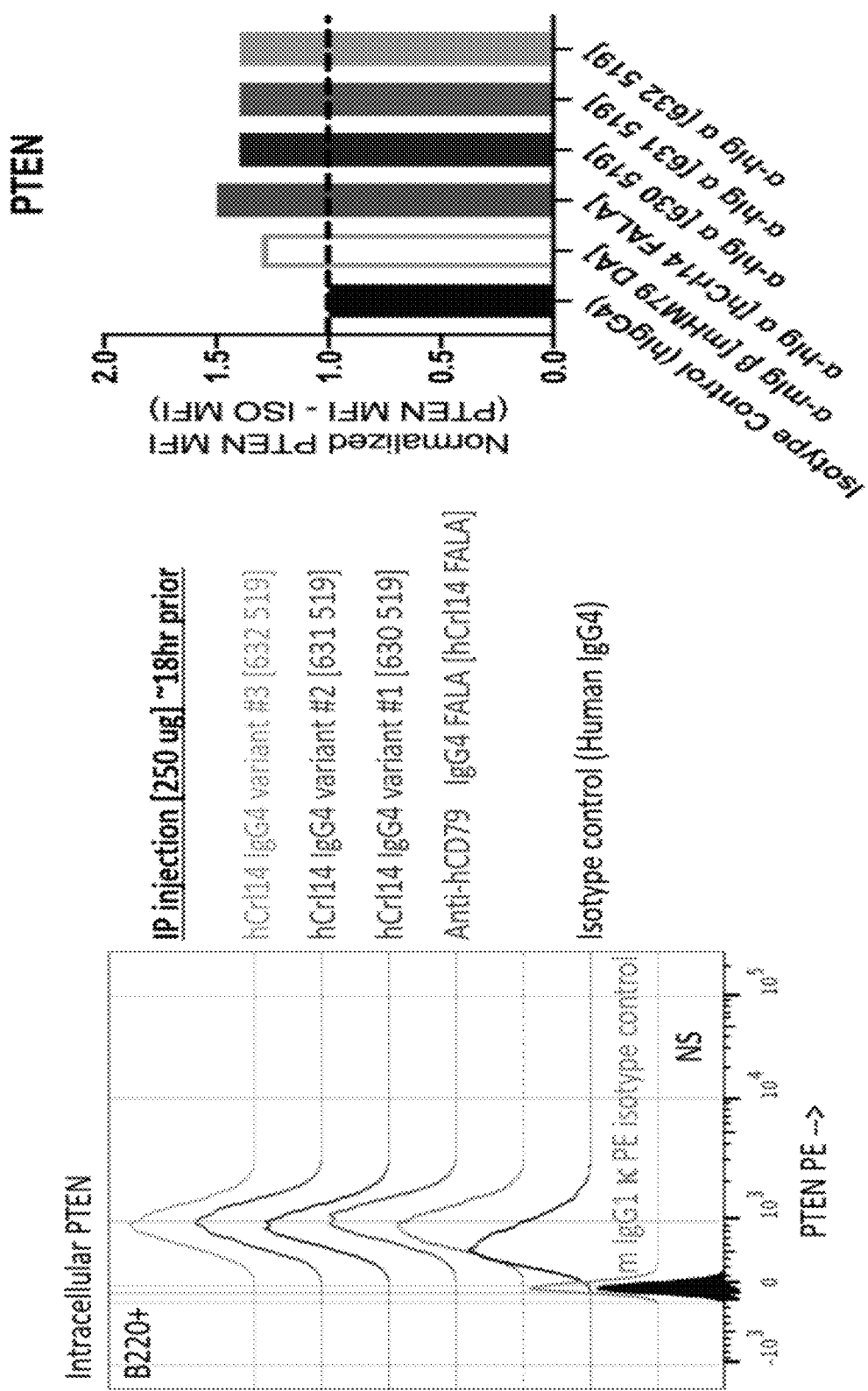
FIG. 3b shows PTEN in B-cells treated with different anti-hCD79 antibodies.
Figure 3C:
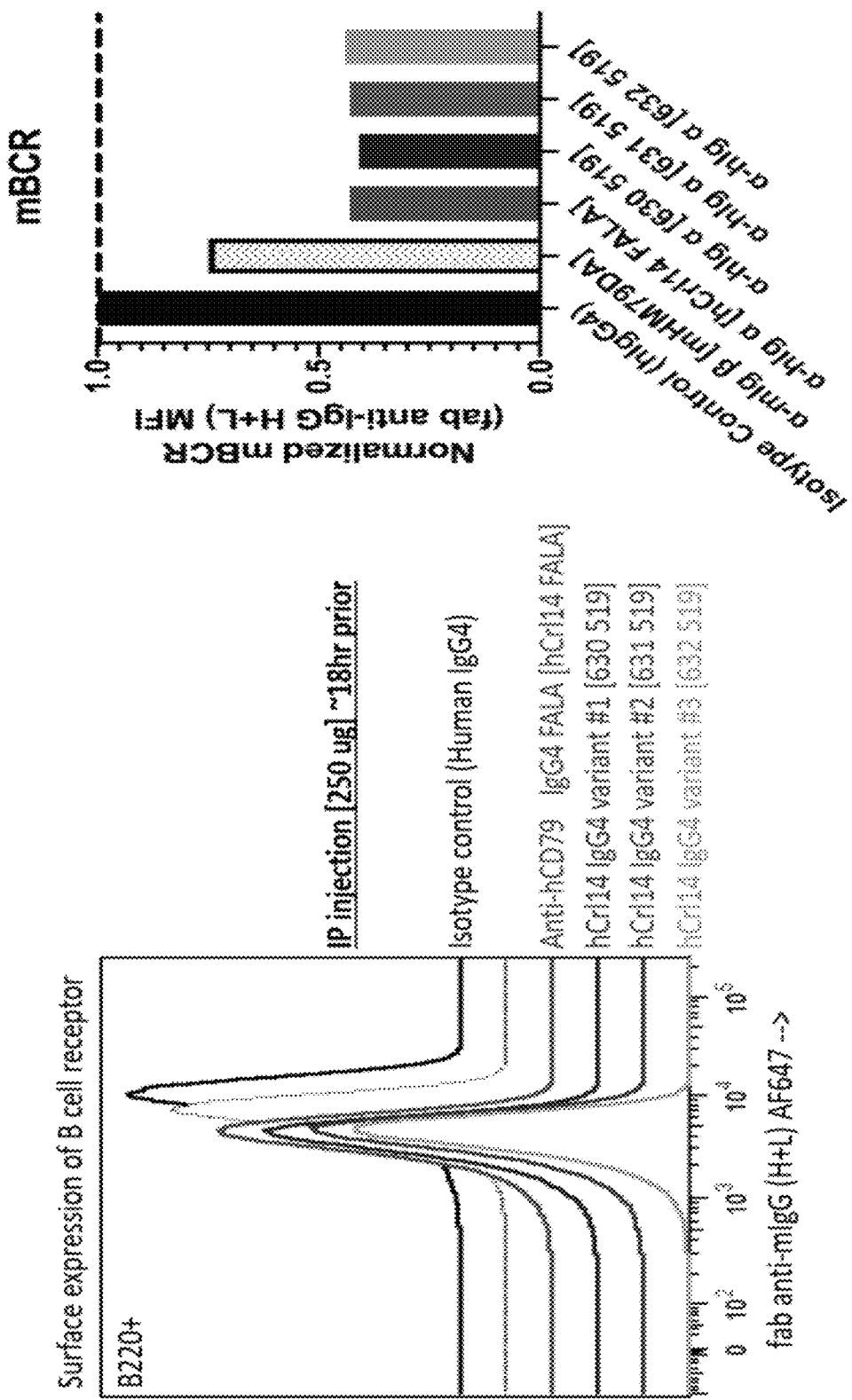
FIG. 3c shows B-cell receptor (BCR) expression after treatment of B-cells with different anti-hCD79 antibodies.

Example 7. Anti-CD79 Antibody Induced Anergy of B-Cells in Human CD79 C57BL/6 Mice The human CD79 knockin mice were treated with humanized anti-CD79 antibody LB517/LB519 for 18 hours before the assays. Ex vivo, RBC-lysed splenocytes (1E6/100 µL) were then stained with anti-B220 and fluorescently labeled Anti-hCD79, or PTEN, or B cell receptor. The LB517/LB519 (hCurl4 FALA) was able to bind the B cells and compete with Curly-14 (FIG. 3a). The intracellular levels of PTEN and cell surface BCR were also characterized by staining with appropriate antibodies. LB517/LB519 was able to induce PTEN expression (FIG. 3b) and down-regulate BCR expression (FIG. 3c).

Figure 4A:
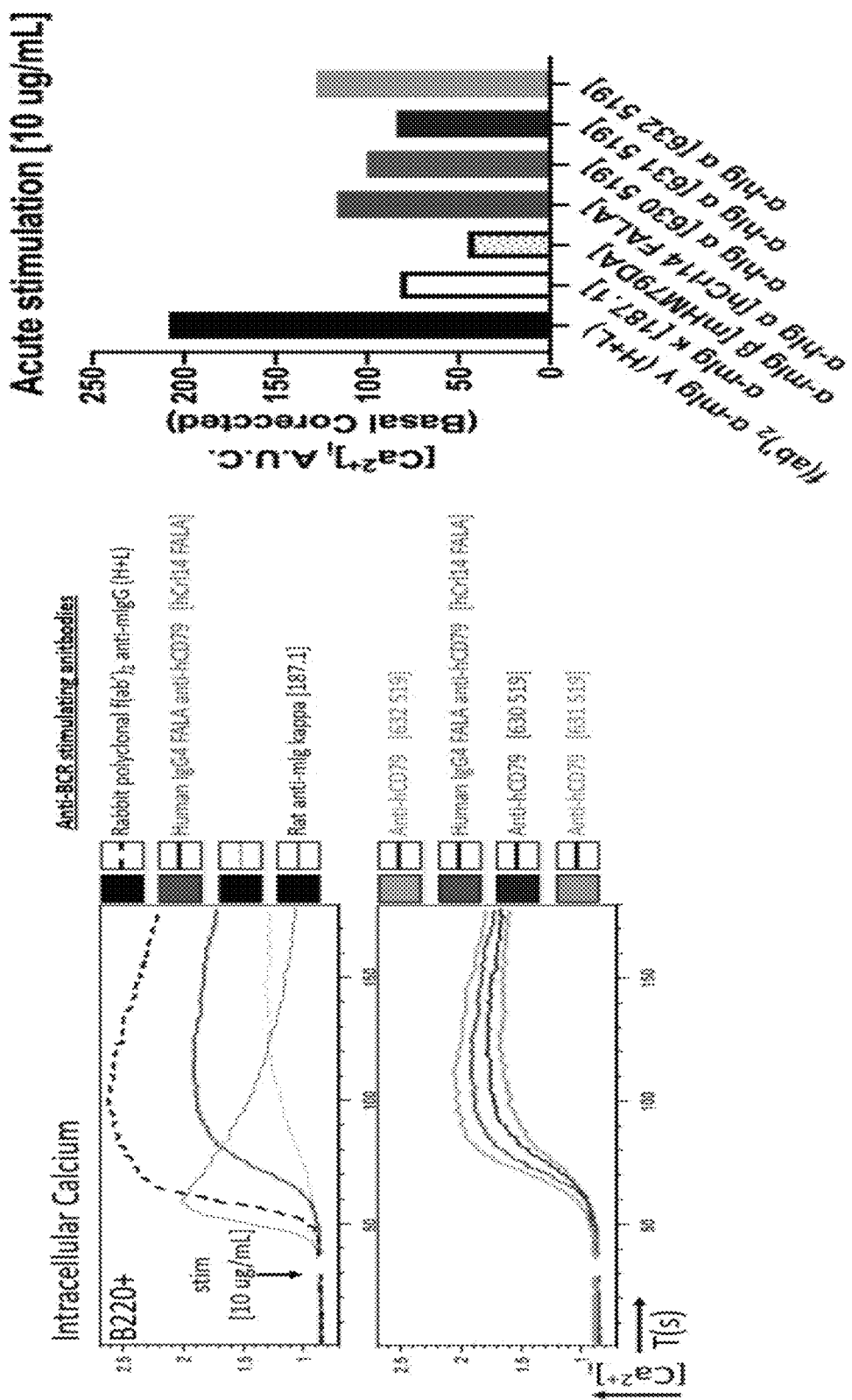
FIG. 4a shows calcium influx in B-cells after treatment with different anti-hCD79 antibodies.
Figure 4B:
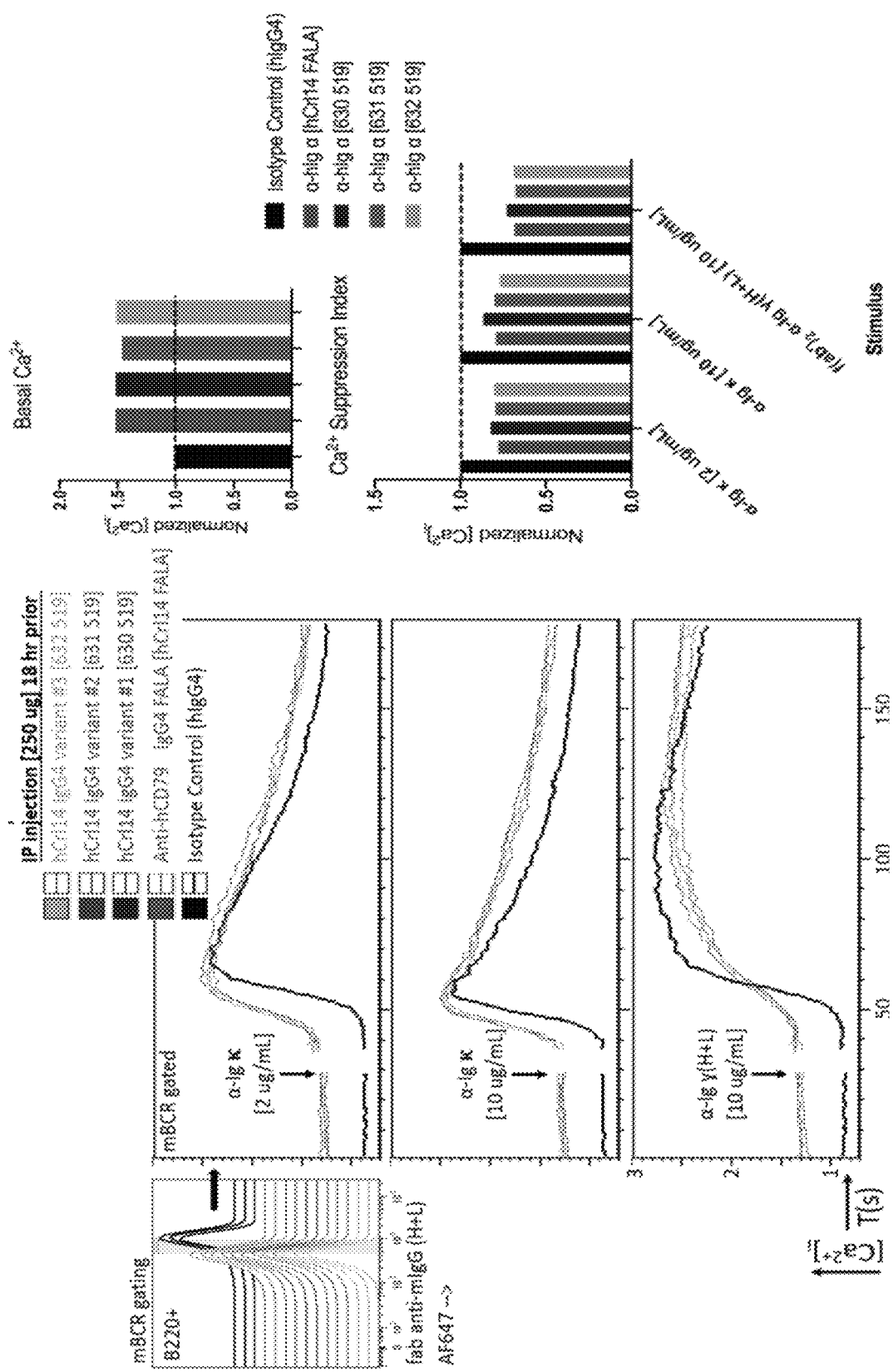
FIG. 4b shows desensitization of the B-cell receptor after treatment of B-cells with different anti-hCD79 antibodies.

The B-cells of these mice were tested for calcium flux upon activation through the B-cell receptor. RBC-lysed splenocytes (1E7/mL) were stained with anti-B220 (B cells) and loaded with a calcium sensing dye (Indo-1 AM) for 1 hour before flow analysis. Changes in intracellular Ca2+ levels were recorded as ratio of fluorescent emissions at 405 nm and 485 nm measure in the FORTESSA (BD Bioscience) running Flow-Jo software (Tree Star). Baseline calcium was acquired for 30 sec before adding stimuli in 100 µL medium. Basal calcium measurements were subtracted from post-stim A.U.C.s in order to generate acute stimulation quantification. The LB517/LB519 stimulated calcium influx (FIG. 4a) and desensitized the B-cell receptors (FIG. 4b).

The B-cells from the C57BL/6 mice were also tested for tyrosine phosphorylation upon B-cell receptor stimulation. These studies showed that pretreatment of the B-cells with humanized anti-CD79 antibody LB517/LB519 desensitized the B-cells to activation through the B-cell receptor as tyrosine phosphorylation was inhibited in the anti-CD79 antibody treated B-cells.

Example 8. Treatment of Type-I Diabetes

Mice expressing the IgM heavy chain transgenes VH125 and VH281 on the NOD and C57BL/6 backgrounds were obtained. VH125.C57BL/6 mice were backcrossed onto the C57BL/6-H2g7 (JAX) to create VH125.C57BL/6.H2g7. Two consecutive blood glucose readings >250 mg/dL (One Touch) identified the VH125.C57BL/6.H2g7 mouse as diabetic.

VH125NOD mice that were pre-diabetic (consecutive blood glucose readings of >150-<200 mg/dL) were treated with anti-CD79 antibody or saline. FIG. 1 shows that the saline treated mice developed type I diabetes (80% by week 5). FIG. 1 also shows that the mice treated with anti-CD79 antibody developed less type I diabetes (25-30% by week 5).

Example 9. Treatment of Type-I Diabetes with Humanized Anti-CD79 Antibody LB517/LB519

C57BL/6 mice expressing human CD79a/b in its B-cells were made according to Example 6. hCD79a/b C57BL/6 mice had PTPn22 R620W knocked into the ROSA26 locus with an intervening floxed stop cassette. Disease is activated in adult mice by tamoxifen-induced cre$^{tam}$ driven expression of the PTPn22 R620W autoimmunity risk allele in conjunction with streptozotocin (STZ) treatment to damage the pancreatic β cells.

Six- to eight-week-old mice are injected (i.p.) with 40 mg/kg of STZ (Sigma-Aldrich) on 4 consecutive days. Blood glucose levels are measured twice weekly using Bayer Contour Meter (Bayer) beginning 2 weeks after the final STZ injection. Diabetes is defined by the elevation of glucose levels >500 mg/dL for 2 consecutive tests.

PTPn22 R620W hCD79a/b C57BL/6 mice are treated with humanized anti-CD79 antibody LB517/LB519 or saline prior/during/after treatment of the mice with STZ. Mice are monitored by blood glucose levels taken twice weekly. Diabetes is defined by the elevation of glucose levels >500 mg/dL for 2 consecutive tests.

Example 10. Treatment of Arthritis

Figure 5:
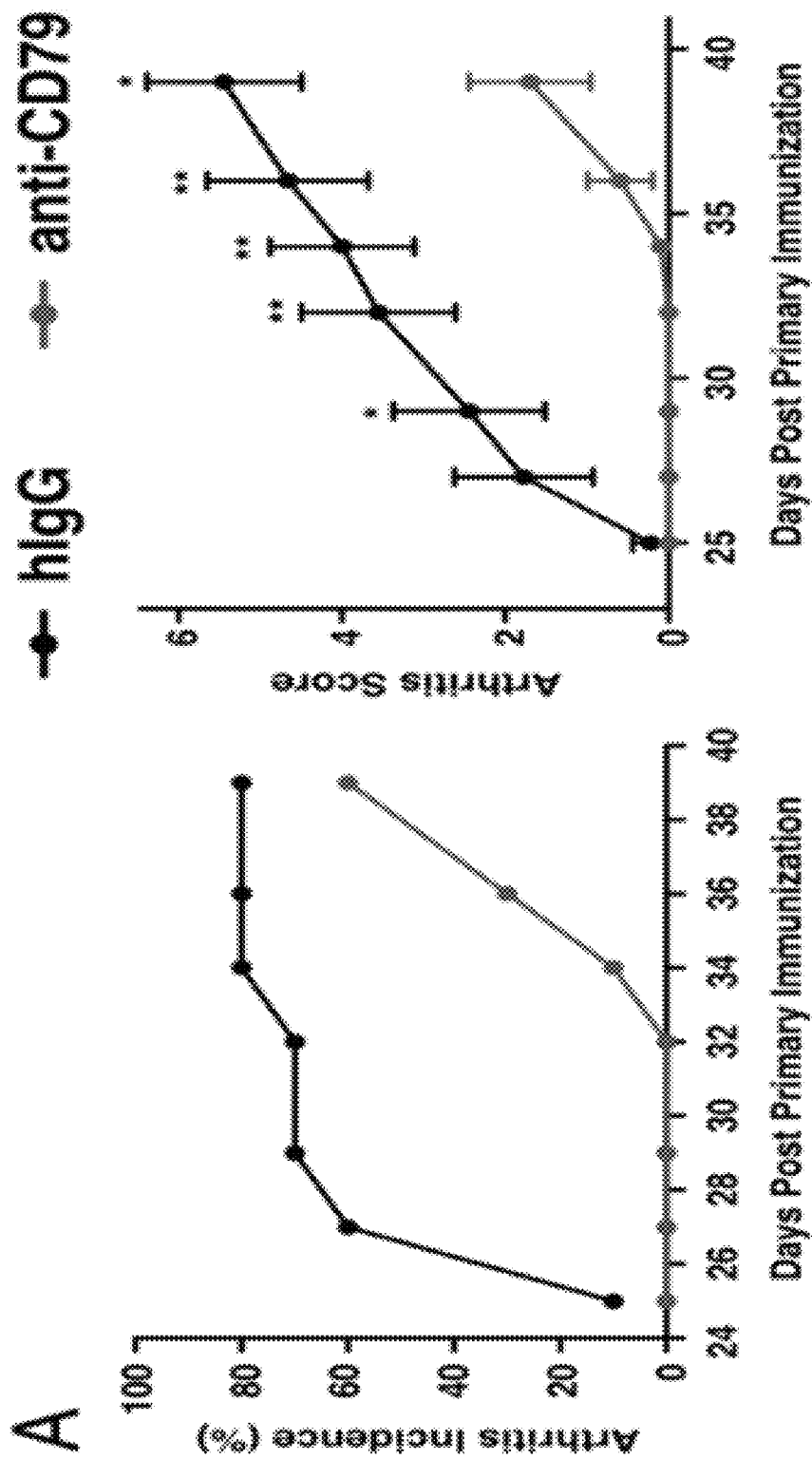
FIG. 5 shows the effect of treatment with anti-hCD79 antibodies on the development of arthritis in an arthritis model system.

C57BL/6 mice were immunized with bovine or chicken Collagen Type II (CII) emulsified in Complete Freund Adjuvant (CFA) at day 0. After 21 days, mice received a secondary immunization with CII emulsified in Incomplete Freund Adjuvant (IFA). 1 mg of anti-CD79 or isotype control immunoglobulins were administered subcutaneously (s.c.) on day 0. Two hours after mAb injection the mice were immunized with collagen. Clinical scores will be assessed after the secondary immunization on individual paws, applying a scale ranging from 0 to 4, as previously described (Hardy, 2014). Anti-CD79 has significantly inhibited the development of arthritis (FIG. 5).

hCD79a/b C57BL/6 mice expressing human CD79a/b in its B-cells were made according to Example 6. hCD79a/b C57BL/6 mice are immunized with bovine or chicken Collagen Type II (CII) emulsified in Complete Freund Adjuvant (CFA) at day 0. After 21 days, mice received a secondary immunization with CII emulsified in Incomplete Freund Adjuvant (IFA).

Anti-mouse CD79 D265A, anti-human CD79 (humanized anti-CD79 antibody LB517/LB519), anti-CD20 (18B12) or isotype control immunoglobulins will be administered subcutaneously (s.c.) on day 0. Two hours after mAb injection the mice were immunized with collagen.

Clinical scores will be assessed after the secondary immunization on individual paws, applying a scale ranging from 0 to 4, as previously described (Hardy, 2014).

Example 11. Treatment of Systemic Lupus

Figure 6:
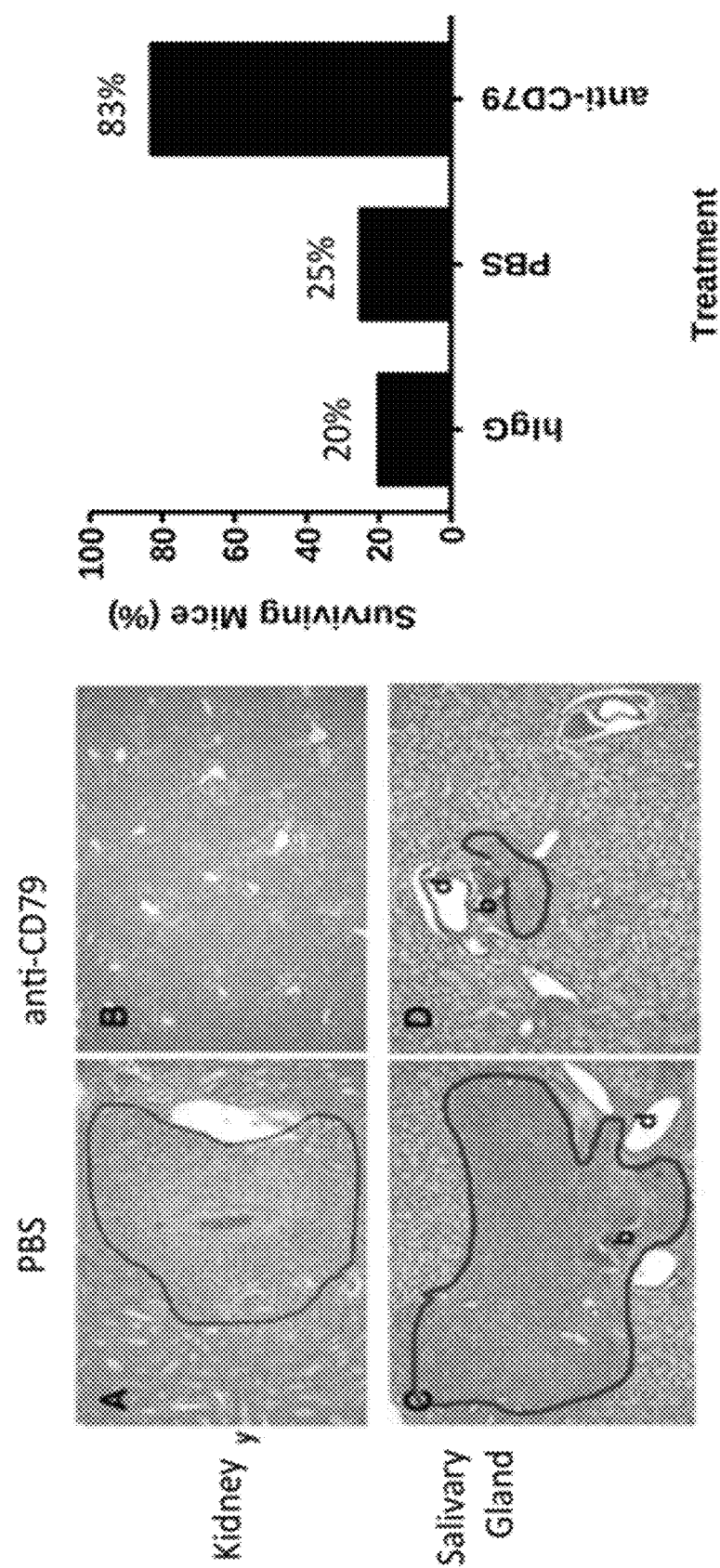
FIG. 6 shows the efficacy of treatment with anti-hCD79 antibodies on the development of lupus in a lupus model system.

MRL/lpr, MRL/lpr-Thy1 0.1 mice were given weekly injections of 0.5 mg of anti-CD79 for 6-17 wk. Anti-CD79 reduced inflammation in kidney and submandibular salivary glands and improves survival at 17 weeks qwk (FIG. 6).

hCD79a/b C57BL/6 mice expressing human CD79a/b in its B-cells were made according to Example 6. hCD79a/b C57BL/6 mice are treated with acute tamoxifen to delete SH2-containing inositol lipid phosphatase (SHIP-1) and/or inositol lipid phosphatase PTEN in B-cells. Getahun et al., J Exp Med. 2016 May 2; 213(5):751-69, which is incorporated by reference in its entirety for all purposes.

Humanized anti-CD79 antibody LB517/LB519, anti-CD20 (18B12), or isotype control immunoglobulin are administered subcutaneously weekly beginning at 8 weeks of age (after autoantibody appearance) in tamoxifen treated human CD79 C57BL6 mice. Production of anti-chromatin autoantibody, glomerular deposition and mouse health will be monitored.

Example 12. Epitope Mapping of Humanized Anti-CD79 Antibodies

The binding epitope of anti-CD79 antibodies are mapped by competition of various fragments of the CD79 antigen and structure analysis.

Example 13. Construction of Anti-CD79 CAR-T for Cancer Treatment

Figure 2:
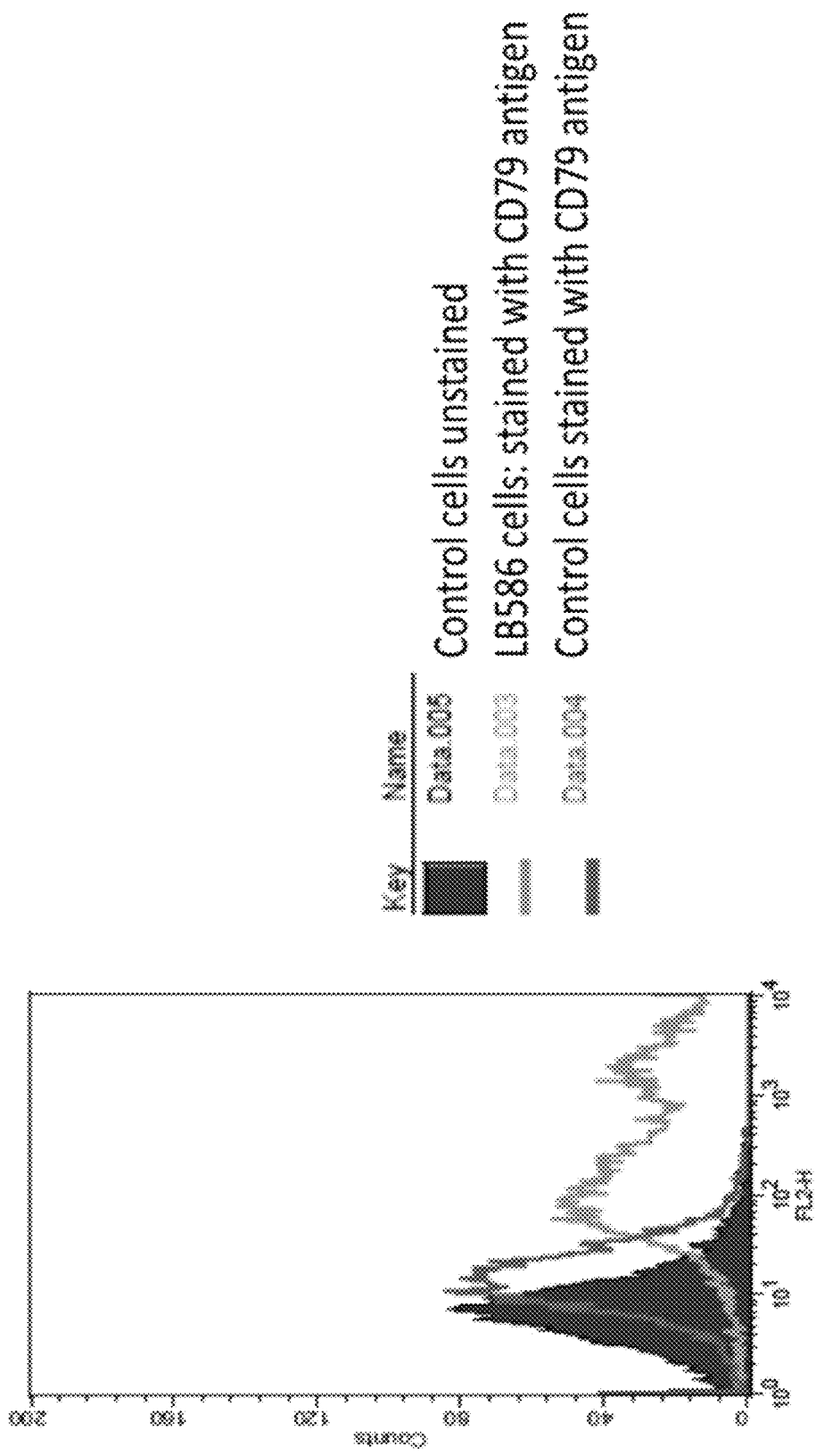
FIG. 2 is a graph showing the binding of soluble CD79 antigen to the cells expressing anti-CD79 CAR-T construct.

The anti-CD79 antibody L1H2 was converted to a scFv antibody and fused to a transmembrane domain, 4-1BB and CD3 zeta intracellular domains in vector LB586. The plasmid LB586 was transfected in CHO cells and selected with appropriate antibiotics for 2 weeks. The stable cells were stained with soluble biotinylated CD79 antigen followed by streptavidin PE conjugate. The binding of CD79 antigen was confirmed by flow cytometry analysis (FIG. 2). The nucleic acid sequence of the anti-CD79 chimeric antigen receptor was:

```
                                            (SEQ ID NO: 69)
GATGTTGTGATGACTCAGTCTCCACTCTCCCTGCCCGTCACCCTTGGACA

GCCGGCCTCCATCTCCTGCAAGTCAAGTCAGAGCCTCTTAGATAGTGATG

GAAAGACATATTTGAATTGGTTACAGCAGAGGCCAGGCCAATCTCCAAGG

CGCCTAATTTATCTGGTGTCTAAACTGGACTCTGGGGTCCCAGACAGATT

CAGCGGCAGTGGGTCAGGCACTGATTTCACACTGAAAATCAGCAGGGTGG

AAGCTGAGGATGTTGGGGTTTATTACTGCTGGCAAGGTACACATCTGCCA

TTCACGTTCGGCGGAGGGACCAAGGTGGAGATCAAAGGTGGCGGTGGCTC

GGGCGGTGGTGGGTCGGGTGGCGGCGGATCTCAGGTGCAGCTGGTGCAGT

CTGGGGCTGAGGTGAAGAAGCCTGGGGCCTCAGTGAAGGTCTCCTGCAAG

GCTTCTGGATACGCATTCAGTTACTCCTGGATGAACTGGGTGCGACAGGC

CCCTGGACAAGGGCTTGAGTGGATGGGACGGATTTATCCTGAAAATGGAG

ATACTAACTACAATGGGAAGTTCAAGGGCAGGGTCACCATGACCAGGGAC

ACGTCCATCAGCACAGCCTACATGGAGCTGAGCAGGCTGAGATCTGACGA

CACGGCCGTGTATTACTGTGCGAGATGGGTCTATGGTCTTCCCCACTTTG

ACTACTGGGGCCAAGGAACCCTGGTCACCGTCTCCTCAGCTAGCACCACG

ACGCCAGCGCCGCGACCACCAACACCGGCGCCCACCATCGCGTCGCAGCC

CCTGTCCCTGCGCCCAGAGGCGTGCCGGCCAGCGGCGGGGGCGCAGTGC

ACACGAGGGGGCTGGACTTCGCCTGTGATATCTACATCTGGGCGCCCTTG

GCCGGGACTTGTGGGGTCCTTCTCCTGTCACTGGTTATCACCCTTTACTG

CAAACGGGGCAGAAAGAAACTCCTGTATATATTCAAACAACCATTTATGA
```

```
                        -continued
GACCAGTACAAACTACTCAAGAGGAAGATGGCTGTAGCTGCCGATTTCCA

GAAGAAGAAGAAGGAGGATGTGAACTGAGAGTGAAGTTCAGCAGGAGCGC

AGACGCCCCGCGTACAAGCAGGGCCAGAACCAGCTCTATAACGAGCTCAA

TCTAGGACGAAGAGAGGAGTACGATGTTTTGGACAAGAGACGTGGCCGGG

ACCCTGAGATGGGGGGAAAGCCGAGAAGGAAGAACCCCCAGGAAGGCCTG

TACAATGAACTGCAGAAAGATAAGATGGCGGAGGCCTACAGTGAGATTGG

GATGAAAGGCGAGCGCCGGAGGGGCAAGGGGCACGATGGCCTTTACCAGG

GTCTCAGTACAGCCACCAAGGACACCTACGACGCCCTTCACATGCAGGCC

CTGCCCCCTCGCTGA
```

The amino acid sequence of the anti-CD79 chimeric antigen receptor was:

```
                                            (SEQ ID NO: 70)
DVVMTQSPLSLPVTLGQPASISCKSSQSLLDSDGKTYLNWLQQRPGQSPR

RLIYLVSKLDSGVPDRFSGSGSGTDFTLKSRVEAEDVGVYYCWQGTHLPF

TFGGGTKVEIKGGGGSGGGGSGGGGSQVQLVQSGAEVKKPGASVKVSCKA

SGYAFSYSWMNWVRQAPGQGLEWMGRIYPENGDTNYNGKFKGRVTMTRDT

SISTAYMELSRLRSDDTAVYYCARWVYGLPHFDYWGQGTLVTVSSASTTT

PAPRPPTPAPTIASQPLSLRPEACRPAAGGAVHTRGLDFACDIYIWAPLA

GTCGVLLLSLVITLYCKRGRKKLLYIFKQPFMRPVQTTQEEDGCSCRFPE

EEEGGCELRVKFSRSADAPAYKQGQNQLYNELNLGRREEYDVLDKRRGRD

PEMGGKPRRKNPQEGLYNELQKDKMAEAYSEIGMKGERRRGKGHDGLYQG

LSTATKDTYDALHMQALPPR
```

The anti-CD79 CAR-T vector is used to make cytotoxic T-cells to treat CD79 positive cancers.

Example 14. Treatment of Multiple Sclerosis

Figure 7:
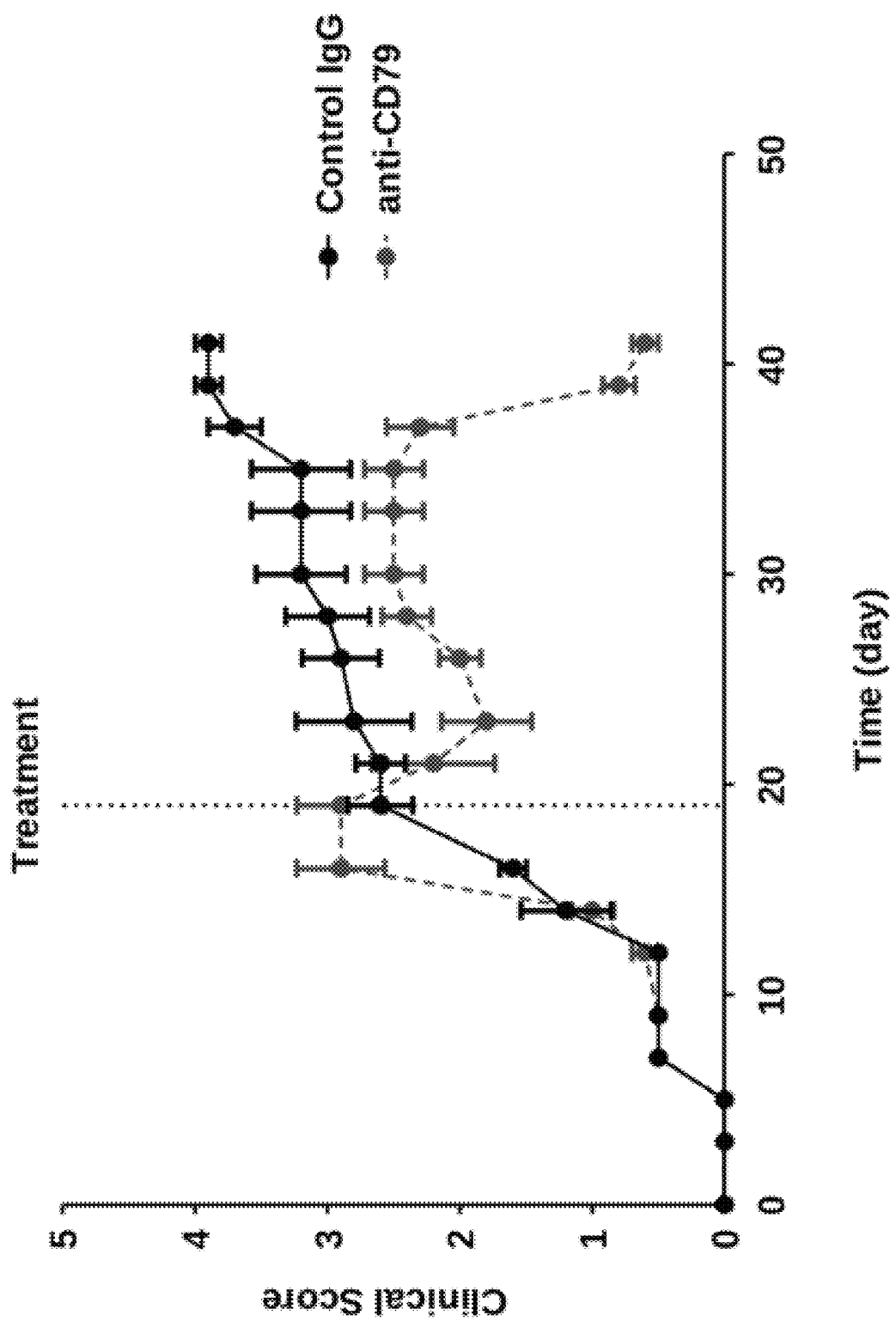
FIG. 7 shows the efficacy of treatment with anti-hCD79 antibodies on the development of multiple sclerosis in a model system for MS.

C57BL6/J mice were immunized according to a standard protocol using 200 μg myelin oligodendrocyte glycoprotein (MOG) 35-55 emulsified in 200 μL Complete Freund's Adjuvant (CFA). The emulsion was injected subcutaneously at two sites followed by two intraperitoneal (i.p.) injections of 200 ng pertussis toxin (PTX) in phosphate buffered saline (PBS), the first 1-2 h after MOG35-55, and the second 24 h thereafter. 1 mg of anti-CD79 was administered weekly starting at day 19. EAE scores and body weights were assessed daily to evaluate the severity and stage of the disease. Treatment of anti-CD79 attenuated progression of the disease model (FIG. 7).

Example 15. Engineering of Affinity-Matured Humanized Antibody LB517/519

There are 2 "NG" motif in the VH CDR2 (SEQ ID NO: 4) which correlates with high Asn deamidation propensity leading to production complication. The Asn residues could be mutated to eliminate the deamidation risk if the mutation does not affect the antigen interaction negatively. The first NG motif was engineered to NS (SEQ ID NO: 75) and cloned into expression vector LB630. The second NG motif was engineered to NA (SEQ ID NO: 76) and cloned into expression vector LB631. Both NG motif were engineered (SEQ ID NO: 77) and cloned into expression vector LB632.

(SEQ ID NO: 75)
QVQLVQSGAEVKKPGASVKVSCKASGYAFSYSWMNWVRQAPGQGLEWMGR

IYPESGDTNYNGKFKGRVTMTRDTSISTAYMELSRLRSDDTAVYYCARWV

YGLPHFDYWGQGTLVTVSS

SEQ ID NO: 75 was designated LB630.

(SEQ ID NO: 76)
QVQLVQSGAEVKKPGASVKVSCKASGYAFSYSWMNWVRQAPGQGLEWMGR

IYPENGDTNYAGKFKGRVTMTRDTSISTAYMELSRLRSDDTAVYYCARWV

YGLPHFDYWGQGTLVTVSS

SEQ ID NO: 76 was designated LB631.

(SEQ ID NO: 77)
QVQLVQSGAEVKKPGASVKVSCKASGYAFSYSWMNWVRQAPGQGLEWMGR

IYPESGDTNYAGKFKGRVTMTRDTSISTAYMELSRLRSDDTAVYYCARWV

YGLPHFDYWGQGTLVTVSS

SEQ ID NO: 77 was designated LB632.

After pairing with the light chain expression vector LB519, the engineered antibodies were produced and purified from 293 cells by transient transfection. The antigen binding kinetics was characterized and presented in Table 3 below:

TABLE 3

Binding Affinity for Affinity Matured Antibodies

| Loading Sample ID | KD (M) | Kon (1/Ms) | Kdis (1/s) | Full X^2 | Full R^2 |
|---|---|---|---|---|---|
| PRI43/PRI47 | 9.22E−09 | 4.17E+04 | 3.84E−04 | 0.8803 | 0.9934 |
| LB517/519 | 7.06E−10 | 5.87E+04 | 4.14E−05 | 0.6118 | 0.9964 |
| LB630/519 | <1.0E−12 | 5.58E+04 | <1.0E−07 | 0.6271 | 0.9972 |
| LB631/519 | 1.04E−09 | 5.86E+04 | 6.10E−05 | 0.3757 | 0.9982 |
| LB632/519 | 8.37E−10 | 6.10E+04 | 5.11E−05 | 0.3287 | 0.9983 |

Among 3 engineered antibodies, LB631/519 and LB632/519 had slightly less potent binding comparing to LB517/519, whereas LB630/519 had much improved antigen binding.

The bioactivities of these engineered antibodies were characterized similarly as in Example 7. The engineered antibodies exhibited similar B-cells desensitization activities comparing to LB517/519 (FIGS. 3 and 4).

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that all aspects of the disclosure are not limited to the specific depictions, configurations or relative proportions set forth herein, which may depend upon a variety of conditions and variables. Various modifications and variations in form and detail of the embodiments and examples of the disclosure will be apparent to a person skilled in the art. It is therefore contemplated that the disclosure also covers any and all such modifications, variations and equivalents.

We claim:

1. An anti-CD79 antibody comprising a heavy chain with a variable region selected from the group consisting of SEQ ID NOs: 9-17, 24-27, 32-41, 71, 72, and 75-77, a light chain with a variable region selected from the group consisting of SEQ ID NOs: 18-23, 28-31, 42-56, and 73-74.

2. The anti-CD79 antibody of claim 1, wherein the variable region of the heavy chain is selected from the group consisting of SEQ ID NOs: 24-27, 71, 75-77 and the variable region of the light chain is selected from the group consisting of SEQ ID NOs: 28-31.

3. The antibody of claim 2, wherein the variable region of the heavy chain is a SEQ ID NO: 25 and the variable region of the light chain is a SEQ ID NO: 30.

4. The antibody of claim 2, wherein the variable region of the heavy chain is a SEQ ID NO: 75 and the variable region of the light chain is a SEQ ID NO: 30.

5. The antibody of claim 2, wherein the variable region of the heavy chain is a SEQ ID NO: 76 and the variable region of the light chain is a SEQ ID NO: 30.

6. The antibody of claim 2, wherein the variable region of the heavy chain is a SEQ ID NO: 77 and the variable region of the light chain is a SEQ ID NO: 30.

7. The antibody of claim 2, wherein the variable region of the heavy chain is a SEQ ID NO: 25 and the variable region of the light chain is a SEQ ID NO: 28.

8. The antibody of claim 2, wherein the variable region of the heavy chain is a SEQ ID NO: 25 and the variable region of the light chain is a SEQ ID NO: 29.

9. The antibody of claim 6, wherein the variable region of the heavy chain is a SEQ ID NO: 25 and the variable region of the light chain is a SEQ ID NO: 31.

10. An anti-CD79 antibody comprising a heavy chain with a variable region chain selected from a group consisting of a SEQ ID NOs: 9-17, and a light chain with a variable region selected from the groups consisting of a SEQ ID NOs: 18-23.

11. The anti-CD79 antibody of claim 10, wherein the variable region of the heavy chain is selected from the group consisting of SEQ ID NOs: 9-11 and the variable region of the light chain is selected from the group consisting of SEQ ID NOs: 18-20.

12. The antibody of claim 10, wherein the variable region of the heavy chain is a SEQ ID NO: 9 and the variable region of the light chain is a SEQ ID NO: 19.

13. The antibody of claim 10, wherein the variable region of the heavy chain is a SEQ ID NO: 10 and the variable region of the light chain is a SEQ ID NO: 19.

* * * * *